US008882757B2

(12) United States Patent
Muller et al.

(10) Patent No.: US 8,882,757 B2
(45) Date of Patent: Nov. 11, 2014

(54) EYE THERAPY SYSTEM

(75) Inventors: David Muller, Boston, MA (US);
Radha Pertaub, Somerville, MA (US);
Steven Meyers, Waltham, MA (US);
Russ Dresher, Marlborough, MA (US);
Thomas Ryan, Waltham, MA (US);
Ronald Scharf, Waltham, MA (US)

(73) Assignee: Avedro, Inc., Waltham, MA (US)

( * ) Notice: Subject to any disclaimer, the term of this patent is extended or adjusted under 35 U.S.C. 154(b) by 411 days.

(21) Appl. No.: 12/617,554

(22) Filed: Nov. 12, 2009

(65) Prior Publication Data
US 2010/0185192 A1     Jul. 22, 2010

Related U.S. Application Data

(60) Provisional application No. 61/113,395, filed on Nov. 11, 2008.

(51) Int. Cl.
*A61B 18/18*        (2006.01)
*A61F 9/007*        (2006.01)
*A61B 19/00*        (2006.01)

(52) U.S. Cl.
CPC ........... *A61B 18/18* (2013.01); *A61B 2019/465* (2013.01); *A61F 9/0079* (2013.01); *A61B 18/1815* (2013.01)
USPC .............................................. 606/33; 606/41

(58) Field of Classification Search
USPC ......... 604/291; 606/166, 33; 607/53, 98–100, 607/109, 115
See application file for complete search history.

(56) References Cited

U.S. PATENT DOCUMENTS

| 3,073,310 A | 1/1963 | Mocarski |
| 3,776,230 A | 12/1973 | Neefe |
| 4,043,342 A | 8/1977 | Morrison, Jr. |

(Continued)

FOREIGN PATENT DOCUMENTS

| EP | 1 561 440 | 8/2005 |
| EP | 1 790 383 | 5/2007 |

(Continued)

OTHER PUBLICATIONS

Chandonnet, CO2 Laser Annular Thermokeratoplasty: A Preliminary Study, Lasers in Surgery and Medicine 12:264-273 (1992), Wiley-Lill, Inc.

(Continued)

*Primary Examiner* — Linda Dvorak
*Assistant Examiner* — Thomas Giuliani
(74) *Attorney, Agent, or Firm* — McDonnell Boehnen Hulbert & Berghoff LLP

(57) ABSTRACT

Systems and methods improve operation of an applicator that delivers heat-generating energy to an eye as a part of an eye therapy. For example, reflected power may be measured to determine whether sufficient contact has been established between the applicator and the eye for accurate and precise delivery of energy to the eye. In addition, at least one of forward and reflected power may be measured to monitor the application of coolant pulses that control the generation of heat in the eye when the applicator delivers energy to the eye. Further, the forward and reflected power may be measured to determine an efficiency of energy transfer or an impedance mismatch. Based on the efficiency of energy transfer or the impedance mismatch, an adjustable parameter of a tuning element may be modified.

12 Claims, 19 Drawing Sheets

(56) References Cited

U.S. PATENT DOCUMENTS

| | | |
|---|---|---|
| 4,326,529 A | 4/1982 | Doss et al. |
| 4,381,007 A | 4/1983 | Doss |
| 4,429,960 A | 2/1984 | Mocilac et al. |
| 4,481,948 A | 11/1984 | Sole |
| 4,490,022 A | 12/1984 | Reynolds |
| 4,546,773 A | 10/1985 | Kremer et al. |
| 4,712,543 A | 12/1987 | Baron |
| 4,743,725 A | 5/1988 | Risman |
| 4,796,623 A | 1/1989 | Krasner et al. |
| 4,805,616 A | 2/1989 | Pao |
| 4,881,543 A | 11/1989 | Trembly et al. |
| 4,891,043 A | 1/1990 | Zeimer et al. |
| 4,943,296 A | 7/1990 | Funakubo et al. |
| 4,994,058 A | 2/1991 | Raven et al. |
| 5,019,074 A | 5/1991 | Muller |
| 5,080,660 A | 1/1992 | Buelna |
| 5,103,005 A | 4/1992 | Gyure et al. |
| 5,123,422 A | 6/1992 | Charvin |
| 5,171,254 A | 12/1992 | Sher |
| 5,281,211 A | 1/1994 | Parel et al. |
| 5,332,802 A | 7/1994 | Kelman et al. |
| 5,368,604 A | 11/1994 | Kilmer et al. |
| 5,370,644 A | 12/1994 | Langberg |
| 5,395,385 A | 3/1995 | Kilmer et al. |
| 5,437,658 A | 8/1995 | Muller et al. |
| 5,461,212 A | 10/1995 | Seiler et al. |
| 5,490,849 A | 2/1996 | Smith |
| 5,586,134 A | 12/1996 | Das et al. |
| 5,591,185 A | 1/1997 | Kilmer et al. |
| 5,618,284 A | 4/1997 | Sand |
| 5,624,456 A | 4/1997 | Hellenkamp |
| 5,626,595 A | 5/1997 | Sklar et al. |
| 5,634,921 A | 6/1997 | Hood et al. |
| 5,658,278 A | 8/1997 | Imran et al. |
| 5,695,448 A | 12/1997 | Kimura et al. |
| 5,766,171 A | 6/1998 | Silvestrini |
| 5,779,696 A | 7/1998 | Berry et al. |
| 5,814,040 A | 9/1998 | Nelson et al. |
| 5,830,139 A | 11/1998 | Abreu |
| 5,873,901 A | 2/1999 | Wu et al. |
| 5,885,275 A | 3/1999 | Muller |
| 5,910,110 A | 6/1999 | Bastable |
| 5,919,222 A | 7/1999 | Hjelle et al. |
| 5,938,674 A | 8/1999 | Terry |
| 5,941,834 A | 8/1999 | Skladnev et al. |
| 6,033,396 A | 3/2000 | Huang et al. |
| 6,036,688 A | 3/2000 | Edwards |
| 6,053,909 A | 4/2000 | Shadduck |
| 6,101,411 A | 8/2000 | Newsome |
| 6,104,959 A | 8/2000 | Spertell |
| 6,110,182 A | 8/2000 | Mowlai-Ashtiani |
| 6,120,434 A | 9/2000 | Kimura et al. |
| 6,139,876 A | 10/2000 | Kolta |
| 6,149,646 A | 11/2000 | West, Jr. et al. |
| 6,161,544 A | 12/2000 | DeVore et al. |
| 6,162,210 A | 12/2000 | Shadduck |
| 6,213,997 B1 | 4/2001 | Hood et al. |
| 6,293,938 B1 | 9/2001 | Muller |
| 6,319,273 B1 | 11/2001 | Chen et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,419,671 B1 | 7/2002 | Lemberg |
| 6,520,956 B1 | 2/2003 | Huang |
| 6,617,963 B1 | 9/2003 | Watters et al. |
| 6,749,604 B1 | 6/2004 | Eggers et al. |
| 6,918,906 B2 | 7/2005 | Long |
| 6,946,440 B1 | 9/2005 | DeWoolfson |
| 7,044,945 B2 | 5/2006 | Sand |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,402,562 B2 | 7/2008 | DeWoolfson |
| 7,651,506 B2 | 1/2010 | Bova et al. |
| 7,713,268 B2 | 5/2010 | Trembly |
| 7,875,024 B2 | 1/2011 | Turovskiy et al. |
| 7,976,542 B1 | 7/2011 | Cosman et al. |
| 8,177,778 B2 | 5/2012 | Muller et al. |
| 8,202,272 B2 | 6/2012 | Muller et al. |
| 8,348,935 B2 | 1/2013 | Muller et al. |
| 8,398,628 B2 | 3/2013 | Muller |
| 8,409,189 B2 | 4/2013 | Muller |
| 2001/0021844 A1 | 9/2001 | Kurtz et al. |
| 2001/0034502 A1 | 10/2001 | Moberg et al. |
| 2001/0039422 A1 | 11/2001 | Carol et al. |
| 2002/0002369 A1 | 1/2002 | Hood |
| 2002/0013579 A1 | 1/2002 | Silvestrini |
| 2002/0022873 A1 | 2/2002 | Erickson et al. |
| 2002/0035345 A1 | 3/2002 | Beck |
| 2002/0049437 A1 | 4/2002 | Silvestrini |
| 2002/0077699 A1 | 6/2002 | Olivieri et al. |
| 2002/0091323 A1 | 7/2002 | Dreher |
| 2002/0091401 A1 | 7/2002 | Hellenkamp |
| 2002/0099363 A1 | 7/2002 | Woodward et al. |
| 2002/0143326 A1 | 10/2002 | Foley et al. |
| 2002/0164379 A1 | 11/2002 | Nishihara et al. |
| 2003/0018255 A1 | 1/2003 | Martin et al. |
| 2003/0097130 A1 | 5/2003 | Muller et al. |
| 2003/0167061 A1 | 9/2003 | Schlegel et al. |
| 2003/0175259 A1 | 9/2003 | Karageozian |
| 2003/0181903 A1 | 9/2003 | Hood et al. |
| 2003/0216728 A1 | 11/2003 | Stern et al. |
| 2004/0001821 A1 | 1/2004 | Silver et al. |
| 2004/0002640 A1 | 1/2004 | Luce |
| 2004/0049186 A1 | 3/2004 | Hood et al. |
| 2004/0111086 A1 | 6/2004 | Trembly |
| 2004/0143250 A1* | 7/2004 | Trembly .................. 606/33 |
| 2004/0199158 A1 | 10/2004 | Hood et al. |
| 2004/0243160 A1 | 12/2004 | Shiuey et al. |
| 2005/0033202 A1 | 2/2005 | Chow et al. |
| 2005/0070977 A1 | 3/2005 | Molina |
| 2005/0131401 A1 | 6/2005 | Malecki et al. |
| 2005/0183732 A1* | 8/2005 | Edwards .................. 128/898 |
| 2005/0197657 A1 | 9/2005 | Goth et al. |
| 2005/0241653 A1 | 11/2005 | Van Heugten et al. |
| 2005/0267332 A1 | 12/2005 | Paul et al. |
| 2005/0287217 A1 | 12/2005 | Levin et al. |
| 2006/0135957 A1 | 6/2006 | Panescu |
| 2006/0149343 A1 | 7/2006 | Altshuler et al. |
| 2006/0189964 A1 | 8/2006 | Anderson et al. |
| 2006/0206110 A1 | 9/2006 | Knowlton et al. |
| 2006/0254851 A1 | 11/2006 | Karamuk |
| 2006/0287649 A1* | 12/2006 | Ormsby et al. .................. 606/33 |
| 2006/0287662 A1 | 12/2006 | Berry et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0074730 A1 | 4/2007 | Nanduri et al. |
| 2007/0114946 A1 | 5/2007 | Goetze et al. |
| 2007/0123845 A1 | 5/2007 | Lubatschowski |
| 2007/0161976 A1 | 7/2007 | Trembly |
| 2007/0179564 A1 | 8/2007 | Harold |
| 2007/0191909 A1 | 8/2007 | Ameri et al. |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2008/0015660 A1 | 1/2008 | Herekar |
| 2008/0027328 A1 | 1/2008 | Klopotek et al. |
| 2008/0300590 A1 | 12/2008 | Horne et al. |
| 2009/0024117 A1 | 1/2009 | Muller |
| 2009/0054879 A1 | 2/2009 | Berry |
| 2009/0069798 A1 | 3/2009 | Muller et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0187173 A1 | 7/2009 | Muller |
| 2009/0187178 A1 | 7/2009 | Muller et al. |
| 2009/0209954 A1 | 8/2009 | Muller et al. |
| 2009/0275936 A1 | 11/2009 | Muller |
| 2010/0094197 A1 | 4/2010 | Marshall et al. |
| 2010/0094280 A1 | 4/2010 | Muller |

(56) References Cited

U.S. PATENT DOCUMENTS

| | | | |
|---|---|---|---|
| 2010/0256626 | A1 | 10/2010 | Muller et al. |
| 2010/0256705 | A1 | 10/2010 | Muller et al. |
| 2010/0280509 | A1 | 11/2010 | Muller et al. |
| 2013/0131664 | A1 | 5/2013 | Muller et al. |

FOREIGN PATENT DOCUMENTS

| | | |
|---|---|---|
| EP | 2 269 531 | 1/2011 |
| WO | WO 99/17690 | 4/1999 |
| WO | WO 00/09027 | 2/2000 |
| WO | 0074648 A2 | 12/2000 |
| WO | WO 03/002008 | 1/2003 |
| WO | WO 2004/033039 | 4/2004 |
| WO | WO 2004/052223 | 6/2004 |
| WO | 2006128038 A2 | 11/2006 |
| WO | WO 2007/022993 | 3/2007 |
| WO | 2007/120457 A2 | 10/2007 |
| WO | WO 2008/008330 | 1/2008 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Muller et al., Br. J. Opthalmol 2001; 85:437-443 (April).
Naoumidi et al., J. Cataract Refract Surg. May 2006; 32(5):732-41.
Pallikaris et al., J. Cataract Refract Surg. Aug. 2005; 31(8):1520-29.
Acosta et al., Cornea. Aug. 2006;25(7):830-8.
Written Opinion corresponding to International Patent Application Serial No. PCT/ US2009/064189, United States Patent Office; dated Jan. 11, 2010 (8 pages).
Search Report corresponding to International Patent Application Serial No. PCT/ US2009/064189, United States Patent Office; dated Jan. 11, 2010 (2 pages).
International Preliminary Report on Patentability corresponding to International Patent Application Serial No. PCT/ US2009/064189, United States Patent Office; dated May 17, 2011 (9 pages).
International Search Report for PCT/US2010/029806 dated Jun. 1, 2010 (3 pages).
Written Opinion for PCT/US2010/029806 dated Jun. 1, 2010 (6 pages).
International Search Report for PCT/US2010/029791 dated Jun. 1, 2010 (3 pages).
Written Opinion for PCT/US2010/029791 dated Jun. 1, 2010 (6 pages).
Trembly et al.; Microwave Thermal Keratoplasty for Myopia: Keratoscopic Evaluation in Procine Eyes; Journal of Refractive Surgery; vol. 17; Nov./Dec. 2001; (8 pages).
Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).
Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).
Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).
Andreassen TT, Simonsen AH, Oxlund H, "Biomechanical Properties of Keratoconus and Normal Corneas," *Experimental Eye Research*, vol. 31, Oct. 1980, pp. 435-441 (7 pages).
Anschutz T, "Laser Correction of Hyperopia and Presbyopia," *International Ophthalmology Clinics*, vol. 34, No. 4, Fall 1994, pp. 107-137 (33 pages).
Bailey MD, Zadnik K, "Outcomes of LASIK for Myopia With FDA-Approved Lasers," *Cornea*, vol. 26, No. 3, Apr. 2007, pp. 246-254 (9 pages).

Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).
Bower KS, Weichel ED, Kim TJ, "Overview of Refractive Surgery," *Am Fam Physician*, vol. 64, No. 7, Oct. 2001, pp. 1183-1190 (8 pages).
Braun EH, Lee J, Steinert RF, "Monovision in LASIK," *Ophthalmology*, vol. 115, No. 7, Jul. 2008, pp. 1196-1202 (7 pages).
Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).
Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).
Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).
Charman WN, "The Eye in Focus: Accommodation and Presbyopia," *Clinical and Experimental Optometry*, vol. 91, May 2008, pp. 207-225 (19 pages).
Corbett et al, "Effect of Collagenase Inhibitors on Coreal Haze after PRK", Exp. Eye Res., vol. 72, Issue 3, pp. 253-259, dated Jan. 29, 2001 (7 pages).
Cox CA, Krueger RR, "Monovision with Laser Vision Correction," *Ophthalmology Clinics of North Amermica*, vol. 19, No. 1, Mar. 2006, pp. 71-75 (7 pages).
Doss JD, Albillar JI, "A Technique for the Selective Heating of Corneal Stroma," *Contact & Intraocular Lens Medical Journal*, vol. 6, No. 1, Jan.-Mar. 1980, pp. 13-17 (8 pages).
Elsheikh A, Anderson K, "Comparative Study of Corneal Strip Extensometry and Inflation Tests," *Journal of the Royal Society Interface*, vol. 2, May 2005, pp. 177-185 (10 pages).
Evans BJW, "Monovision: a Review," *Ophthalmic and Physiological Optics*, vol. 27, Jan. 2007, pp. 417-439 (23 pages).
Gasset AR, Kaufman HE, "Thermokeratoplasty in the Treatment of Keratoconus," *American Journal of Ophthalmology*, vol. 79, Feb. 1975, pp. 226-232 (8 pages).
Gloster J, Perkins ES, "The Validity of the Imbert-Flick Law as Applied to Applanation Tonometry," *Experimental Eye Research*, vol. 2, Jul. 1963, pp. 274-283 (10 pages).
Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).
Hamilton DR, Hardten DR, Lindstrom RL, "Thermal Keratoplasty," *Cornea*, $2^{nd}$ Edition, Chapter 167, 2005, pp. 2033-2045 (13 pages).
Hersh PS, "Optics of Conductive Keratoplasty: Implication for Presbyopia Management," *Transactions of the American Ophthalmological Society*, vol. 103, 2005, pp. 412-456 (45 pages).
Hjortdal JO, "Extensibility of the Normo-Hydrated Human Cornea," *Acta Ophthalmologica Scandinavica*, vol. 73, No. 1, Feb. 1995, pp. 12-17 (7 pages).
Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).
Illueca C, Alió JL, Mas D, Ortiz D, Pérez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).
Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).
Tin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).
Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).

(56) References Cited

OTHER PUBLICATIONS

Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).

Louie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).

Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).

McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).

McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).

Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).

Nash IS, Greene PR, Foster CS, "Comparison of Mechanical Properties of Keratoconus and Normal Corneas," *Experimental Eye Research*, vol. 35, 1982, pp. 413-424 (12 pages).

Newman JM, "Analysis, Interpretation, and Prescription for the Ametropias and Heterophorias," *Borish's Clinical Refraction*, 1998, pp. 776-822 (49 pages).

Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).

Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).

Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).

Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).

Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).

Pinsky PM, Datye DV, "Numerical Modeling of Radial, Astigmatic, and Hexagonal Keratotomy," *Refractive and Conical Surgery*, vol. 8, No. 2, Mar.-Apr. 1992, pp. 164-172 (11 pages).

Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).

Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).

Rosenbloom A, "New Aged and Old Aged: Impact of the Baby Boomer," *Journal of the American Optometry Association*, vol. 74, No. 4, Apr. 2003, pp. 211-213 (5 pages).

Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).

Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).

Seiler T, Matallana M, Bende T, "Laser Thermokeratoplasty by Means of a Pulsed Holmium:YAG Laser for Hyperopic Correction," *Refractive and Corneal Surgery*, vol. 6, No. 5, Sep.-Oct. 1990, pp. 335-339 (6 pages).

Seiler T, Matallana M, Sendler S, Bende T, "Does Bowman's Layer Determine the Biomechanical Properties of the Cornea?" *Refractive and Conical Surgery*, vol. 8, No. 2, Mar.-Apr. 1992, pp. 139-142 (6 pages).

Shin TJ, Vito RP, Johnson LW, McCarey BE, "The Distribution of Strain in the Human Cornea," *Journal of Biomechanics*, vol. 30, No. 5, May 1997, pp. 497-503 (7 pages).

Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).

Stanley PF, Tanzer DJ, Schallhorn SC, "Laser Refractive Surgery in the United States Navy," *Current Opinion Ophthalmology*, vol. 19, Jul. 2008, pp. 321-324 (4 pages).

Strenk SA, Strenk LM, Koretz JF, "The Mechanism of Presbyopia," *Progress in Retinal Eye Research*, vol. 24, May 2005, pp. 379-393 (15 pages).

Stringer H, Parr J., "Shrinkage Temperature of Eye Collagen," *Nature*, Dec. 1964, p. 1307 (1 page).

Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).

Telandro A., "Pseudo-Accommodation Cornea: A New Concept for Correction of Presbyopia," *Journal of Refractive Surgery*, vol. 20, No. 5, Sep.-Oct. 2004, pp. S714-S717 (5 pages).

Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).

Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).

Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).

Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-1111 (7 pages).

Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).

Wollensak, G., et al., "Riboflavin/Ultraviolet-A-Induced Collagen Crosslinking for the Treatment of Keratoconus," *American Journal of Ophthalmology*, Ophthalmic Publ., Chicago, IL, US, vol. 135, No. 5, May 1, 2003, pp. 620-627 (8 pages).

Zelichowska B, Rekas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).

Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.

Berjano et. al.; "Ring Electrode for Radio-Frequency Heating of the Cornea: Modelling and In Vitro Experiments"; Medical & Biological Engineering & Computing 2003; vol. 41; pp. 630-639.

International Search Report mailed Aug. 14, 2009 for PCT/US2009/042204, (5 pages).

International Search Report mailed Nov. 20, 2009 for PCT/2009/059061 (3 pages).

International Search Report mailed Nov. 6, 2009 for PCT/US2009/057481 (2 pages).

European Search Report and Written Opinion for EP 09826739, European Patent Office; dated Feb. 12, 2014 (8 pages).

Morlet N., Minassian D., Dart J., "Astigmatism and the analysis of its surgical correction", Br f Ophthalmol 2001; 85: pp. 1127-1138.

\* cited by examiner

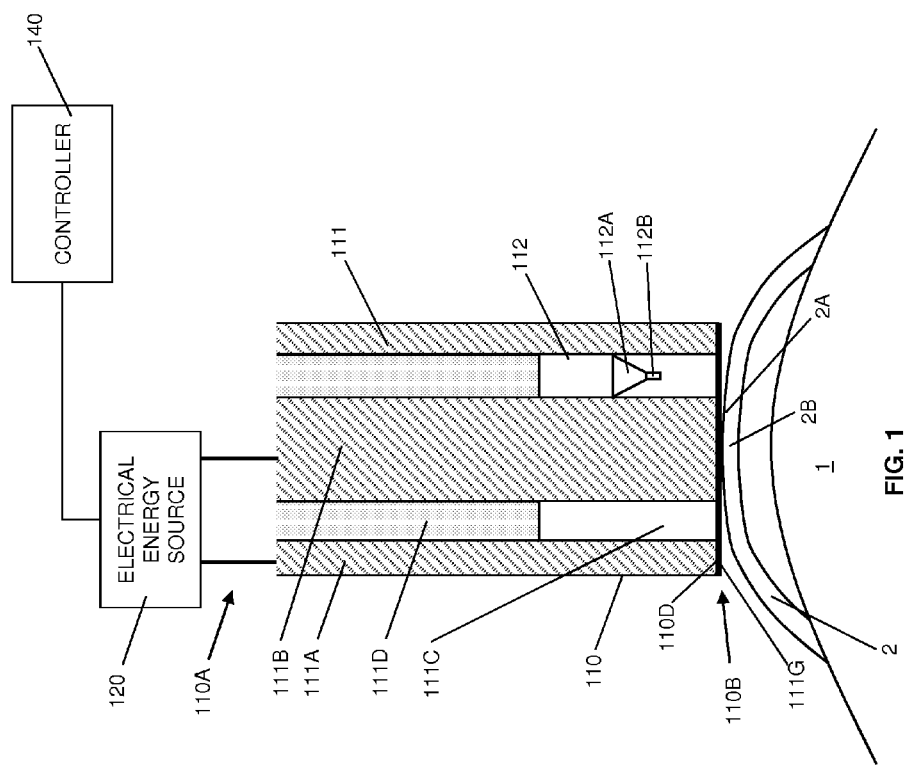

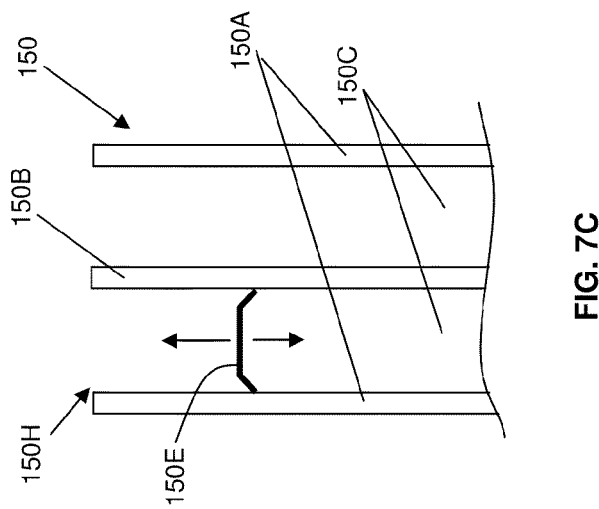
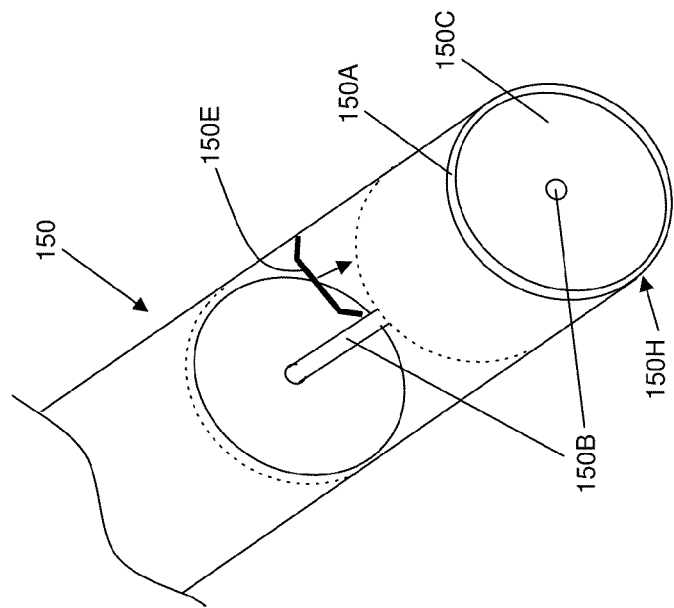
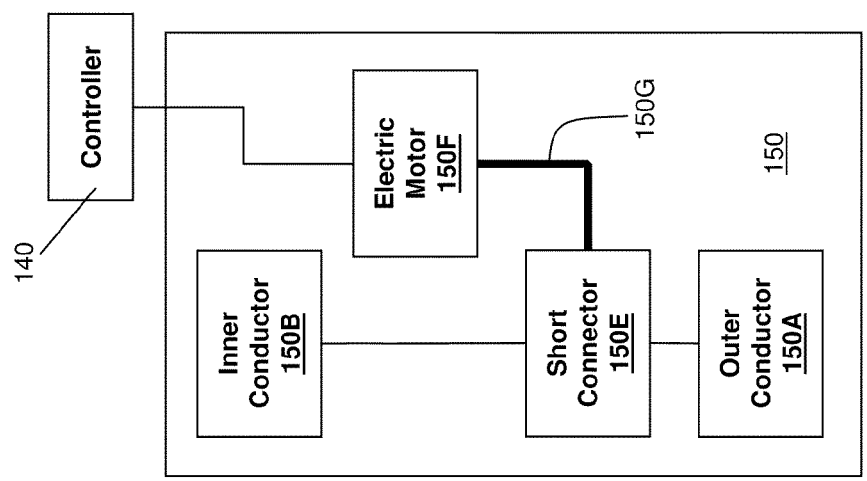

EYE THERAPY SYSTEM

CROSS-REFERENCE TO RELATED APPLICATIONS

This application claims priority to U.S. Provisional Application No. 61/113,395, filed Nov. 11, 2008, the contents of which are incorporated entirely herein by reference.

BACKGROUND OF THE INVENTION

1. Field of the Invention

The invention pertains to the field of keratoplasty and, more particularly, to the application of a device configured to treat one or more eye disorders by causing corrective reshaping of an eye feature.

2. Description of Related Art

A variety of eye disorders, such as myopia, keratoconus, and hyperopia, involve abnormal shaping of the cornea or the eye itself. Keratoplasty reshapes the cornea to correct such disorders. For example, with myopia, the cornea may be too steep or the eyeball too long, causing the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratomileusis (LASIK), may be employed to reshape the cornea. However, such surgical procedures typically require a healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy in the microwave or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy in circular or ring-shaped patterns may cause aspects of the cornea to flatten and improve vision in the eye.

SUMMARY OF THE INVENTION

Embodiments according to aspects of the present invention provide systems and methods that improve operation of an applicator that delivers heat-generating energy to an eye as a part of an eye therapy. An example method comprises positioning a distal end of an applicator at or proximate to a surface of an eye, supplying an amount of energy from an energy source to the applicator to apply therapy to the eye, a first portion of the energy supplied to the applicator being transmitted through the distal end to the eye and a second portion of the energy supplied to the applicator being reflected from the distal end of the applicator, detecting a signal corresponding to the reflected energy, and determining an amount of contact based on the signal. A corresponding example system comprises an energy source, an applicator, and a dual directional coupler, one or more of the components of the system being configured to carry out one or more steps of the method.

The example method may further include one or more of the steps of: ceasing supply of energy to the applicator based on the amount of contact; after ceasing supply of energy, moving the applicator towards the surface of the eye, and resuming supply of energy to the applicator; and moving the applicator towards the eye until a desired amount of contact is determined based on the signal corresponding to the reflected energy.

The example method may further include one or more of the following characteristics: the amount of contact includes no contact; the signal corresponding to the reflected energy has a power and the method further comprises detecting a decrease in the power; the signal corresponding to the reflected energy has a power and the method further comprises detecting an increase in the power; the signal corresponding to the reflected energy has a power that decreases as the amount of contact increases; the signal corresponding to the reflected energy has a power and the method further comprises determining whether the power is less than a threshold value; the signal corresponding to the reflected energy has a power that increases as the amount of contact increases; the signal corresponding to the reflected energy has a power and the method further comprises determining whether the power is greater than a threshold value; the applicator comprises a conducting element, the conducting element being configured to conduct energy from the energy source to apply therapy to an eye, and a covering configured to be removably attached to the conducting element, the covering having an interface surface positionable at the eye, at least a portion of the interface surface including one or more dielectric materials, the energy from the conducting element being deliverable to the eye through the interface surface; the covering forms an enclosure over a portion of the conducting element and the applicator further comprises a coolant delivery system, the coolant delivery system being operable to deliver coolant within the enclosure to cool the interface surface of the covering and the eye, and the enclosure preventing the coolant from directly contacting the eye; the detecting is performed by a dual directional coupler; and the energy supplied to the applicator is a microwave energy.

Another example method comprises positioning a distal end of an applicator at or proximate to an eye, supplying an amount of energy to the applicator from an energy source to apply therapy to the eye, a first portion of the energy supplied to the applicator being transmitted through the distal end to the eye and a second portion of the energy supplied to the applicator being reflected from the distal end, supplying a coolant pulse to the eye, and detecting a signal corresponding to at least one of the energy supplied to the applicator and the energy reflected from the distal end, the signal further corresponding to the coolant pulse. A corresponding example system comprises an energy source, an applicator, a coolant delivery system operable to deliver coolant to cool the eye, and a dual directional coupler, one or more of the components of the system being configured to carry out one or more steps of the method.

The example method may further include one or more of the following characteristics: the applicator comprises a conducting element, the conducting element being configured to conduct energy from the energy source to apply therapy to an eye, a covering configured to be removably attached to the conducting element, the covering having an interface surface positionable at the eye, at least a portion of the interface surface including one or more dielectric materials, the energy from the conducting element being deliverable to the eye through the interface surface, the covering forming an enclosure over a portion of the conducting element, and a coolant delivery system, the coolant delivery system being operable to deliver coolant within the enclosure to cool the interface surface of the covering and the eye, and the enclosure preventing the coolant from directly contacting the eye; the signal corresponds to the energy supplied to the applicator, the signal having a power, the power decreasing when coolant is delivered to the interface surface; the signal corresponds to the energy reflected from the distal end of the applicator, the signal having a power, the power increasing when coolant is delivered to the interface surface; the detecting is performed by a dual directional coupler; and the energy supplied to the applicator is a microwave energy.

Yet another method comprises supplying an amount of energy from an energy source to a distal end of an applicator to apply therapy to an eye, a first portion of the energy supplied to the applicator being transmitted through the distal end to the eye and a second portion of the energy supplied to the applicator being reflected from the distal end, detecting a forward signal corresponding to the energy supplied to the applicator, detecting a reflected signal corresponding to the reflected energy, determining an efficiency of energy transfer based on the forward signal and the reflected signal, and based on the efficiency of energy transfer, modifying at least one adjustable parameter of a tuning element corresponding to the applicator. A corresponding example system comprises an energy source, an applicator, a dual directional coupler, a tuning element, and one or more controllers, one or more of the components of the system being configured to carry out one or more steps of the method.

The method may further include one or more of the following characteristics: the determining the efficiency of energy transfer comprises measuring at least one of a magnitude change and a phase change of the forward signal and the reflected signal; the at least one adjustable parameter is an inductance; the at least one adjustable parameter is a capacitance; the at least one adjustable parameter is not modified when the efficiency of energy transfer is determined to be greater than a first threshold value; the tuning element is electrically connected to the applicator in parallel; the tuning element is integral with the applicator; the tuning element comprises an inner conductor, an outer conductor and a short connector, the inner conductor and the outer conductor being concentric cylinders having a gap therebetween, the short connector electrically connecting the inner conductor to the outer conductor, the short connector being axially moveable within the gap; the tuning element further comprises a controller configured to provide signals to a motor, the motor being configured to mechanically move the short connector within the gap; the applicator comprises a conducting element, the conducting element being configured to conduct energy from the energy source to apply therapy to an eye, and a covering configured to be removably attached to the conducting element, the covering having an interface surface positionable at the eye, at least a portion of the interface surface including one or more dielectric materials, the energy from the energy conducting element being deliverable to the eye through the interface surface; a dual directional coupler detects the forward signal and the reflected signal; and the energy supplied to the applicator is a microwave energy.

A further method comprises supplying an amount of energy from an energy source to a distal end of an applicator to apply therapy to an eye, a first portion of the energy supplied to the applicator being transmitted through the distal end to the eye and a second portion of the energy supplied to the applicator being reflected from the distal end, detecting a forward signal corresponding to the energy supplied to the applicator, detecting a reflected signal corresponding to the reflected energy, determining an impedance mismatch between the eye and the applicator based on the forward signal and the reflected signal, and based on the impedance mismatch, modifying at least one adjustable parameter of a tuning element corresponding to the applicator. A corresponding example system comprises an energy source, a dual directional coupler, a tuning element, and one or more controllers, one or more of the components of the system being configured to carry out one or more steps of the method.

The example method may further include one or more of the following characteristics: the determining the impedance mismatch comprises measuring at least one of a magnitude change and a phase change of the forward signal and the reflected signal; the at least one adjustable parameter is an inductance; the at least one adjustable parameter is a capacitance; the at least one adjustable parameter is not modified when the impedance mismatch is determined to be less than a threshold value; the tuning element is electrically connected to the applicator in parallel; the tuning element is integral with the applicator; the tuning element comprises an inner conductor, an outer conductor and a short connector, the inner conductor and the outer conductor being concentric cylinders having a gap therebetween, the short connector electrically connecting the inner conductor to the outer conductor, the short connector being axially moveable within the gap; the applicator comprises a conducting element, the conducting element being configured to conduct energy from the energy source to apply therapy to an eye, and a covering configured to be removably attached to the conducting element, the covering having an interface surface positionable at the eye, at least a portion of the interface surface including one or more dielectric materials, the energy from the energy conducting element being deliverable to the eye through the interface surface; a dual directional coupler detects the forward signal and the reflected signal; and the energy supplied to the applicator is a microwave energy.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 1 illustrates a system for applying heat to a cornea of an eye to cause reshaping of the cornea.

FIG. 7A illustrates a block diagram of a tuning element according to aspects of the present invention.

FIG. 7B illustrates a perspective view of an embodiment of a tuning element according to aspects of the present invention.

FIG. 7C illustrates a cross-section of an embodiment of a tuning element according to aspects of the present invention.

DESCRIPTION

Figure 2A:
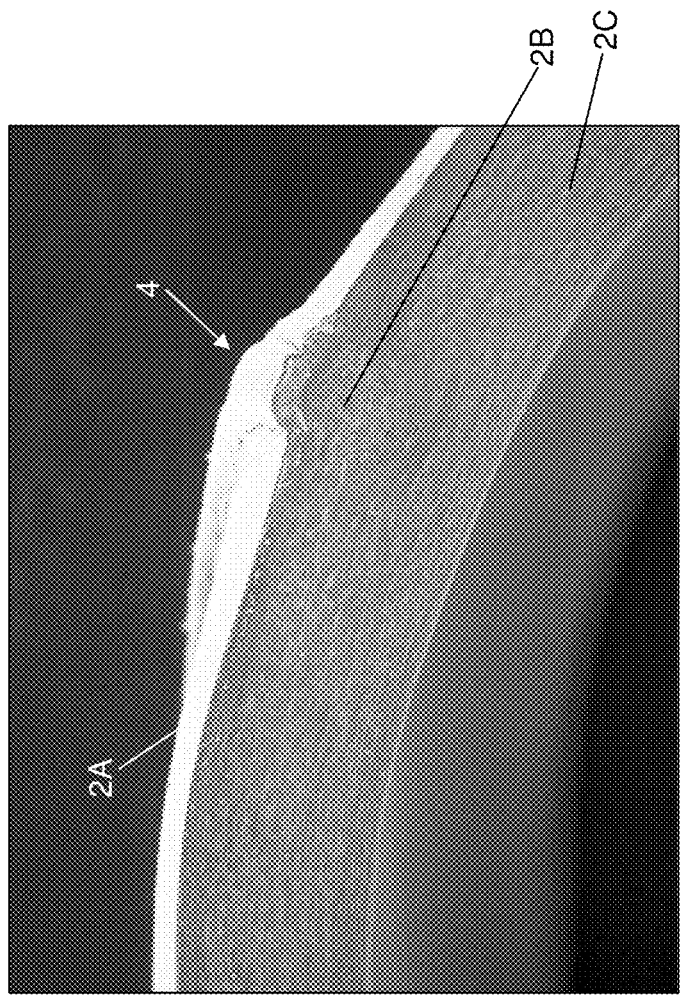
FIG. 2A illustrates a high resolution image of a cornea after heat has been applied.

The embodiments described herein relate to a system and method for improving operation of an applicator that delivers heat-generating energy to an eye as a part of an eye therapy. For example, reflected power is measured to determine whether sufficient contact has been established between the applicator and the eye for accurate and precise delivery of energy to the eye. In addition, at least one of forward and reflected power is measured to monitor the application of coolant pulses that control the generation of heat in the eye when the applicator delivers energy to the eye.

Referring now to the drawings, wherein like reference characters denote similar elements throughout the several views, FIG. 1 illustrates an example system for applying heat to a cornea 2 of an eye 1 to cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply heat energy to the cornea 2, which is positioned at the distal end 110B. In particular, the electrical energy source 120 may include a microwave oscillator for generating microwave energy. For example, the oscillator may operate at a microwave frequency range of 400 MHz to 3000 MHz, and more specifically at a frequency of around 915 MHz or 2450 MHz which has been safely used in other applications. As used herein, the term "microwave" corresponds to a frequency range from about 10 MHz to about 10 GHz.

As further illustrated in FIG. 1, the electrical energy conducting element 111 may include two microwave conductors 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the conductor 111A. With the inner passage, the conductor 111A has a substantially tubular shape. The inner and the outer conductors 111A and 111B may be formed, for example, of aluminum, stainless steel, brass, copper, other metals, coated metals, metal-coated plastic, or any other suitable conductive material.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines the penetration depth of microwave energy into the cornea 2 according to established microwave field theory. Thus, the microwave conducting element 111 receives, at the proximal end 110A, the electrical energy generated by the electrical energy source 120, and directs microwave energy to the distal end 111B, where the cornea 2 is positioned.

The outer diameter of the inner conductor 111B is preferably larger than the pupil. In general, the outer diameter of the inner conductor 111B may be selected to achieve an appropriate change in corneal shape, i.e. keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of heat by the applicator 110.

A controller 140 may be employed to selectively apply the energy any number of times according to any predetermined or calculated sequence. In addition, the heat may be applied for any length of time. Furthermore, the magnitude of heat being applied may also be varied. Adjusting such parameters for the application of heat determines the extent of changes that are brought about within the cornea 2. Of course, the system attempts to limit the changes in the cornea 2 to an appropriate amount of shrinkage of collagen fibrils in a selected region. When employing microwave energy to generate heat in the cornea 2, for example with the applicator 110, the microwave energy may be applied with low power (of the order of 40 W) and in long pulse lengths (of the order of one second). However, other systems may apply the microwave energy in short pulses. In particular, it may be advantageous to apply the microwave energy with durations that are shorter than the thermal diffusion time in the cornea. For example, the microwave energy may be applied in pulses having a higher power in the range of 500 W to 3 KW and a pulse duration in the range of about 10 milliseconds to about one second.

Referring again to FIG. 1, at least a portion of each of the conductors 111A and 111B may be covered with an electrical insulator to minimize the concentration of electrical current in the area of contact between the corneal surface (epithelium) 2A and the conductors 111A and 111B. In some systems, the conductors 111A and 111B, or at least a portion thereof, may be coated with a material that can function both as an electrical insulator as well as a thermal conductor. A dielectric layer 110D may be employed along the distal end 111B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 0.002 inches. In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic, such as polyurethane and silastic, or nonelastic, such as Teflon® and polyimides. The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (thermal conductivity or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

During operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A (or substantially near the corneal surface 2A if there is a thin interposing layer between the conductors 111A and 111B and the corneal surface 2A). Accordingly, direct contact helps ensure that the pattern of microwave heating in the corneal tissue has substantially the same shape and dimension as the gap 111C between the two microwave conductors 111A and 111B.

As shown in FIG. 1, the energy conducting element 111 includes a contact surface 111G that comes into direct contact with the corneal surface 2A. In some cases, for example, where the inner electrode 111B is recessed within the inner passage of the outer conductor 111A, the outer conductor 111A may achieve sufficient contact with the eye 1 while the inner electrode 111B does not have sufficient contact.

In general, the application of energy to the cornea 2 depends in part on the position of the contact surface 111G relative to the corneal surface 2A. As a result, to provide reliable application of energy to the cornea 2, embodiments ensure that the contact surface 111G, or portions thereof, are positioned to make contact with the corneal surface 2A. In this way, the relationship between the energy conducting element 111 and the cornea 2 is more definite and the resulting delivery of energy is more predictable and accurate. Furthermore, safety is enhanced when the applicator 111 is in direct contact with the corneal surface 2A and energy is transferred primarily to the system with good contact. Accordingly, it is preferable not to deliver energy via the energy conducting element 111 unless there is sufficient contact.

In some embodiments, sufficient contact is determined by causing an observable amount of flattening, or applanation, of the cornea. The applanation provides a constant and uniform pressure against the corneal surface 2A. For example, as illustrated in FIG. 1, the applicator 110 can position the energy conducting element 111 against the corneal surface 2A so that the contact surface 111G flattens the cornea 2. Although the contact surface 111G, or portions thereof, in contact with the corneal surface 2A are shown to be substantially flat in FIG. 1, it is understood that the contact surface 111G may be shaped, e.g. contoured, in other ways to cause the desired contact. The applanation described herein adds precision and accuracy to the eye therapy procedure, particularly by improving electrical and thermal contact between the contact surface 111G and the corneal surface 2A.

Other systems and methods for improving electrical and thermal contact between an energy conducting element and the corneal surface are described in U.S. patent application Ser. No. 12/209,123, filed Sep. 11, 2008, which is a continuation-in-part application of U.S. patent application Ser. No. 12/018,457, filed on Jan. 23, 2008, the contents of these applications being entirely incorporated herein by reference. For example, an adjustment system can be employed to improve electrical and thermal contact between the energy conducting element and the corneal surface, as described in further detail below with respect to FIGS. 16-17.

As FIG. 1 also illustrates, the applicator 110 may also include a micro-controlled coolant delivery system 112. The micro-controlled coolant delivery system 112 is in fluid communication with a coolant supply (not shown) and pulses of coolant, or cryogen, from the coolant supply may be applied to the corneal surface 2A before, during, and/or after energy is applied to the cornea 2 with the electrical energy source 120 and the electrical energy conducting element 111. As such, the applicator 110 may be employed to apply coolant to selectively cool the surface 2A of the cornea 2 positioned at the distal end 110B. The delivery of coolant from the coolant delivery element 12 toward the corneal surface 2A, in sequence with the application of heat to the cornea 2, permits the corneal temperature to be increased to cause appropriate shrinkage of the collagen fibers in the targeted mid-depth region 2B and reshape the cornea 2, while also minimizing injury to the outer layer 2A, i.e. the epithelium, of the cornea 2.

The coolant delivery element 112 may have a nozzle structure 112A with an opening 112B directed toward the distal end 110B. Although FIG. 1 may illustrate one nozzle structure 112A, coolant delivery system 112 may include more than one nozzle structure 112A arranged, for example, circumferentially within the annular gap 111C. Although FIG. 1 may illustrate the nozzle structure 112A, other embodiments may employ other types of outlets or ports for delivering coolant to the surface 2A or other areas of the eye 1.

Furthermore, the applicator 110 may define a substantially enclosed assembly at the distal end 110B, which is placed in contact with the corneal surface 2A. As shown in FIG. 1, this enclosed assembly may house the energy conducting element 111 and the coolant delivery element 112. In some embodiments, the dielectric layer 110D may provide a membrane-like layer substantially enclosing the distal end 110B of the applicator 110. In this case, the coolant delivery system 112 applies coolant to the membrane, rather than directly to the eye 1.

The controller 140 may also be operably connected to the coolant delivery element 112 as well as the energy source 120. As such, the controller 140 may be employed to determine the amount and timing of coolant delivered from the coolant delivery element 112 toward the corneal surface 2A at the distal end 110B. The controller 140 may be employed to selectively apply the heat and the coolant any number of times according to a predetermined or calculated sequence. For instance, the coolant may be applied to the corneal surface 2A before, during, or after the application of heat to the cornea 2, or any combination thereof.

In some embodiments, the coolant delivery element 112 may employ a solenoid valve in combination with the delivery nozzle 112A. As is known, a solenoid valve is an electromechanical valve for use with liquid or gas controlled by applying or stopping an electrical current through a coil of wire, thus changing the state of the valve. As such, the controller 140 may electronically control the actuation of the solenoid valve to deliver the coolant through the delivery nozzle 112A to the corneal surface 2A. However, other embodiments may employ other types of actuators or alternative techniques for delivering coolant through the delivery nozzle 112A in place of a solenoid valve.

During operation of the embodiment of FIG. 1, the controller 140 may be used to actuate the application of micro-controlled pulses of coolant to the corneal surface 2A before the application of heat to the cornea 2. A pulse, or a spurt, of coolant is applied to the corneal surface 2A for a predetermined short period of time so that the cooling remains generally localized at the corneal surface 2A while the temperature of deeper corneal collagen fibers 2B remains substantially unchanged. Preferably, the pulse is on the order of milliseconds and is less than 100 milliseconds. The delivery of the coolant to the corneal surface is controlled by the controller 140 and may be less than 1 millisecond. Furthermore, the time between the application of the coolant and the application of the heat is also controlled by the controller 140 and may also be less than 1 millisecond. The coolant pulse generally covers an area of the corneal surface 2A that corresponds with the application of heat to the cornea 2. The shape, size and disposition of the cooled region may be varied according to the application.

Advantageously, localized delivery of coolant to the corneal surface 2A before the application of heat to the cornea 2 minimizes the resulting temperature at the corneal surface 2A when the heat is applied, thereby minimizing any heat-induced injury to the corneal surface 2A. In other words, the coolant reduces the temperature of the corneal surface 2A, so that the maximum surface temperature achieved at the corneal surface 2A during or immediately after heat exposure is also reduced by a similar magnitude when compared to a case where no coolant is applied prior to heat exposure. Without the application of coolant, the temperature at the corneal surface 2A rises during or immediately after heat exposure with persistent surface heating resulting from a slow dissipation of heat trapped near the surface-air interface.

Although temperatures observed at the corneal surface 2A immediately after heat exposure are lowered by the application of coolant before exposure, a delayed thermal wave may arrive at the corneal surface 2A after exposure as the heat generated in the corneal areas 2B below the surface 2A diffuses toward the cooled surface 2A. The heat transfer from the corneal surface 2A to the surrounding air is likely to be insignificant, because air is an excellent thermal insulator. With no cooling after the application of heat, heat diffusing away from the areas 2B beneath the corneal surface 2A builds up near the corneal surface 2A and produces an elevated surface temperature that may persist after the application of heat. Although the heat that builds up near the corneal surface 2A may eventually dissipate through thermal diffusion and cooling via blood perfusion, such dissipation may take several seconds. More immediate removal of this heat by additional application of coolant minimizes the chances for heat-related injury to the corneal surface 2A. Thus, embodiments of may employ not only a pulse of coolant immediately prior to heat exposure, but also one or more pulses of coolant thereafter. Accordingly, in further operation of the embodiment of FIG. 1, the controller 140 may also be used to apply micro-controlled pulses of coolant during or after the applicator 110 applies heat to the cornea 2, or any combination thereof. This application of coolant rapidly removes heat which diffuses from the mid-depth corneal region 2B to the corneal surface 2A.

When the coolant delivery element 12 delivers the pulse of coolant to the corneal surface 2A, the coolant on the corneal surface 2A draws heat from the surface 2A, causing the coolant to evaporate. In general, coolant applied to the surface 2A creates a heat sink at the surface 2A, resulting in the removal of heat before, during, and after the application of heat to the cornea 2. The heat sink persists for as long as the liquid cryogen remains on the surface 2A. The heat sink can rapidly remove the trapped heat at the surface 2A without cooling the collagen fibers in the region 2B. A factor in drawing heat out of the cornea 2 is the temperature gradient that is established near the surface 2A. The steeper the gradient, the faster a given quantity of heat is withdrawn. Thus, the application of the coolant attempts to produce a large surface temperature drop as quickly as possible.

Because the cooled surface 2A provides a heat sink, the amount and duration of coolant applied to the corneal surface 2A affects the amount of heat that passes into and remains in the region underlying the corneal surface 2A. Thus, controlling the amount and duration of the cooling provides a way to control the depth of corneal heating, promoting sufficient heating of targeted collagen fibers in the mid-depth region 2B while minimizing the application of heat to regions outside the targeted collagen fibers.

In general, dynamic cooling of the corneal surface 2A may be optimized by controlling: (1) the duration of the cooling pulse(s); (2) the duty cycle of multiple pulses; (3) the quantity of coolant deposited on the corneal surface 2A so that the effect of evaporative cooling can be maximized; and (4) timing of dynamic cooling relative to heat application. For example, a single pulse timing may include applying a 80 ms heat pulse and a 40 ms cooling pulse at the beginning, middle, or end of the heating pulse. In another example, multiple cooling pulses may be applied according to a pattern of 10 ms ON and 10 ms OFF, with four of these pulses giving a total of 40 ms of cooling, but timed differently.

In some embodiments, the coolant may be the cryogen tetrafluoroethane, $C_2H_2F_4$, which has a boiling point of about −26.5° C. and which is an environmentally compatible, nontoxic, nonflammable freon substitute. The cryogenic pulse released from the coolant delivery element 112 may include droplets of the cryogen cooled by evaporation as well as mist formed by adiabatic expansion of vapor.

In general, the coolant may be selected so that it provides one or more of the following: (1) sufficient adhesion to maintain good surface contact with the corneal surface 2A; (2) a high thermal conductivity so the corneal surface 2A may be cooled very rapidly prior to heat application; (3) a low boiling point to establish a large temperature gradient at the surface; (4) a high latent heat of vaporization to sustain evaporative cooling of the corneal surface 2A; and (5) no adverse health or environmental effects. Although the use of tetrafluoroethane may satisfy the criteria above, it is understood that embodiments of the present invention are not limited to a particular cryogen and that other coolants, such as liquid nitrogen, argon, or the like, may be employed to achieve similar results. For instance, in some embodiments, other liquid coolants with a boiling temperature of below approximately body temperature, 37° C., may be employed. Furthermore, the coolant does not have to be a liquid, but in some embodiments, may have a gas form. As such, the pulse of coolant may be a pulse of cooling gas. For example, the coolant may be nitrogen ($N_2$) gas or carbon dioxide ($CO_2$) gas.

As described previously, the controller 140 may be employed to selectively apply the heat and the coolant pulses any number of times according to any predetermined or calculated sequence. In addition, the heat and the pulses of coolant may be applied for any length of time. Furthermore, the magnitude of heat being applied may also be varied. Adjusting such parameters for the application of heat and pulses of coolant determines the extent of changes that are brought about within the cornea 2. Of course, as discussed, embodiments of the present invention attempt to limit the changes in the cornea 2 to an appropriate amount of shrinkage of selected collagen fibers. When employing microwave energy to generate heat in the cornea 2, for example with the applicator 110, the microwave energy may be applied with low power (of the order of 40 W) and in long pulse lengths (of the order of one second). However, other embodiments may apply the microwave energy in short pulses. In particular, it may be advantageous to apply the microwave energy with durations that are shorter than the thermal diffusion time in the cornea. For example, the microwave energy may be applied in pulses having a higher power in the range of 300 W to 3 kW and a pulse duration in the range of about 2 milliseconds to about one second. Thus, when applying the coolant pulses before and after the application of heat as discussed previously: a first pulse of coolant is delivered to reduce the temperature of the corneal surface 2A; a high power pulse of microwave energy is then applied to generate heat within selected areas of collagen fibers in a mid-depth region 2B; and a second pulse of coolant is delivered in sequence to end further heating effect and "set" the corneal changes that are caused by the energy pulse. The application of energy pulses and coolant pulses in this manner advantageously reduces the amount to heat diffusion that occurs and minimizes the unwanted impact of heating and resulting healing processes on other eye structures, such as the corneal endothelium. Moreover, this technique promotes more permanent and stable change of the shape of the cornea 2 produced by the heat. Although the application of high powered energy in short pulses has been described with respect to the delivery of microwave energy, a similar technique may be applied with other types of energy, such as optical energy or electrical energy with radio frequency (RF) wavelengths described further below.

The system of FIG. 1 is provided for illustrative purposes only, and other systems may be employed to apply energy to generate heat and reshape the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference.

Figure 2B:
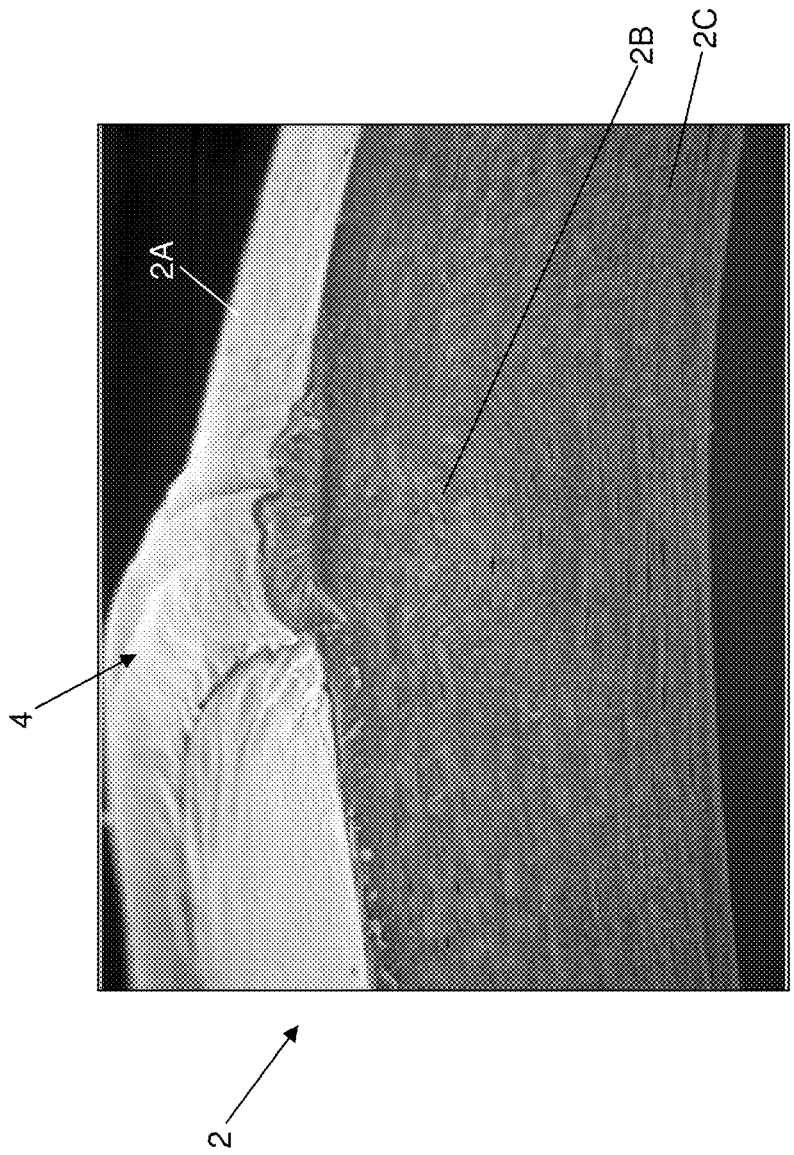
FIG. 2B illustrates another high resolution images of the cornea of FIG. 2A.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in any heat-related damage to the corneal tissue.

Figure 2C:
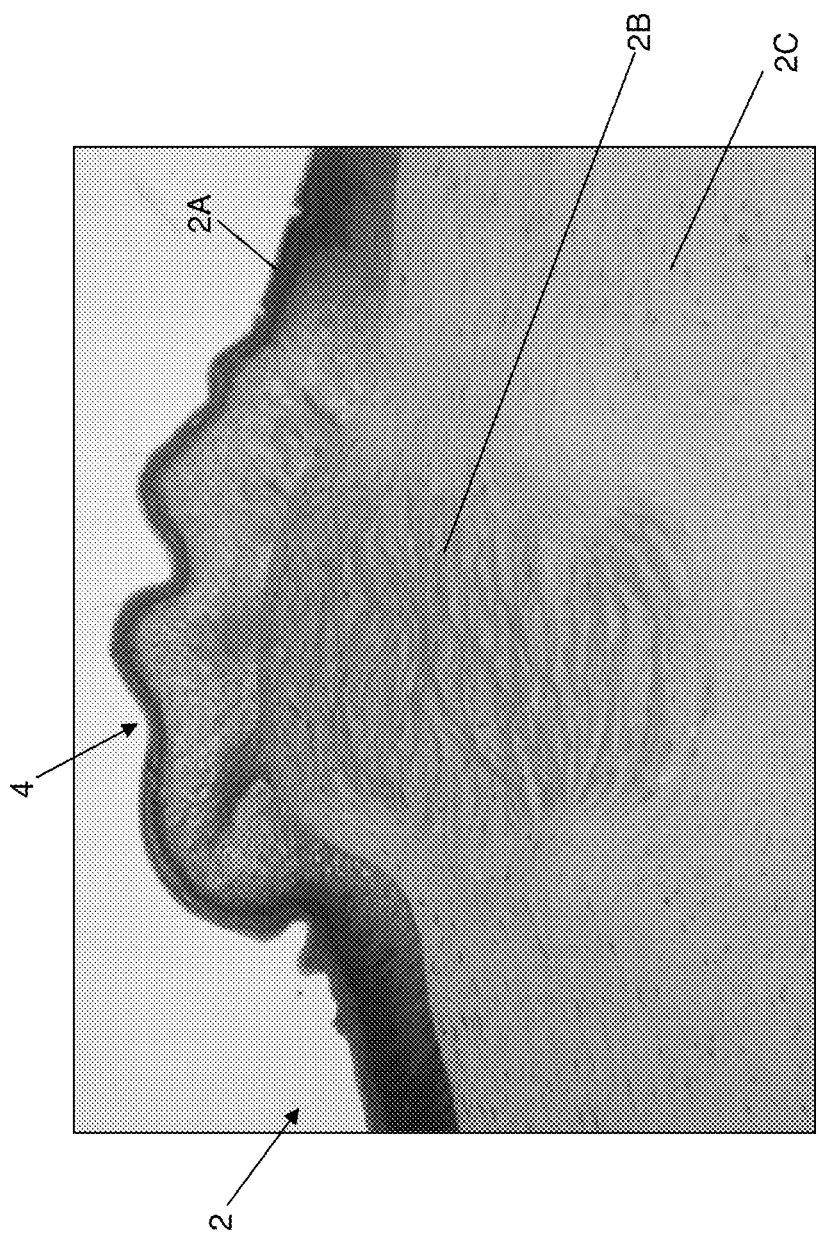
FIG. 2C illustrates a histology image of the cornea of FIG. 2A.
Figure 2D:
FIG. 2D illustrates another histology image of the cornea of FIG. 2A.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, like orthokeratology, which compress areas of the cornea to reshape the cornea via mechanical deformation, the collagen fibrils in the region 2B are in an entirely new state.

Figure 3:
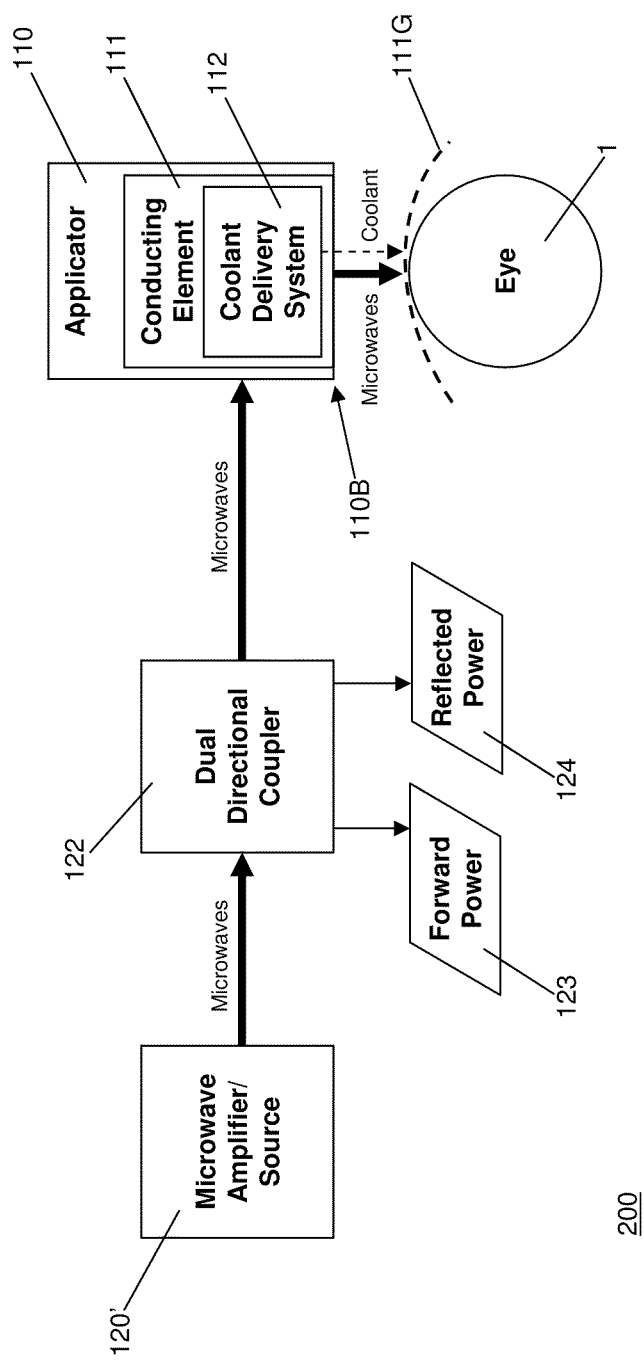
FIG. 3 illustrates an example configuration for a system that determines the contact between the electrical energy conducting element and the eye according to aspects of the present invention.

FIG. 3 illustrates an example configuration for a system 200 that may employ the electrical energy conducting element 111 described previously. The electrical energy conducting element 111 may directly contact the eye 1 with the contact surface 111G. For example, the contact surface 111G may be defined by a membrane-like dielectric layer substantially enclosing the distal end 110B of the applicator 110. In this case, the coolant delivery system 112 applies coolant to the membrane, rather than directly to the eye 1.

As shown in FIG. 3, a microwave amplifier/source 120', which may be controlled by the controller described previously, sends microwave energy to an eye 1 via the electrical energy conducting element 111 which is placed into contact with the eye 1. When the microwaves are delivered through the energy conducting element 111, some microwaves are reflected from the distal end 110B of the energy conducting element 111, and these reflected microwaves have a reflected power. The reflected power generally decreases with increased contact between the energy conducting element 111 and the eye 1. Thus, the net forward power actually delivered to the eye 1 is approximately equal to the difference between the forward power and the reflected power. As further illustrated in FIG. 3, a dual directional coupler 122 may be employed to sample the microwaves and determine the forward power and the reflected power to provide outputs 123 and 124, respectively. In some cases, the outputs 123 and 124 may actually provide levels that are proportional to the initial forward power and the reflected power, respectively. For example, the dual directional coupler 122 may sense the reflected power as a 1/1000 sample of the actual reflected power.

The system 200 of FIG. 3 determines whether the desired contact between the energy conducting element 111 and the eye 1 has been achieved so that the resulting delivery of energy may be applied more predictably and accurately. In particular, when power is initially applied via the energy conducting element 111, the dual directional coupler 122 is employed to determine the reflected power which indicates the level of contact between the energy conducting element 111 and the eye 1. If the reflected power indicates insufficient contact, the system 200 does not further deliver microwaves, for example, through the energy conducting element 111.

The approach of system 200 may be particularly advantageous, because when the applicator 110 is positioned over the eye 1 during operation, the clinician's view of the contact between the energy conducting element 111 and the eye 1 may be obstructed by the applicator 110 itself. Thus, the system 200 allows the clinician to determine whether sufficient contact has been established without requiring visual confirmation. During operation, the clinician monitors the change in reflected power as the applicator 110 is positioned. The change in reflected power indicates the change in contact and applanation and thus allows the clinician to accurately determine the position of the energy conducting element 111.

The system of FIG. 3 is provided for illustrative purposes only. Other systems are described, for example, in U.S. Provisional Patent Application No. 61/098,489, filed Sep. 19, 2008, the contents of which is entirely incorporated herein by reference. As described in U.S. Provisional Patent Application No. 61/098,489, a monitoring system may be employed to monitor both the power delivered to, and reflected from, the eye 1. As described therein, the system may be utilized to extract information on the position of the energy conducting element 111 relative to the eye 1 or on the operation of the cooling delivery system 112. Aspects of the operation of the cooling delivery system 112 are described, for example in example, in U.S. patent application Ser. No. 12/208,963, filed Sep. 11, 2008, which is a continuation-in-part application of U.S. patent application Ser. No. 11/898,189, filed on Sep. 10, 2007, the contents of these applications already being entirely incorporated herein by reference.

Figure 4:
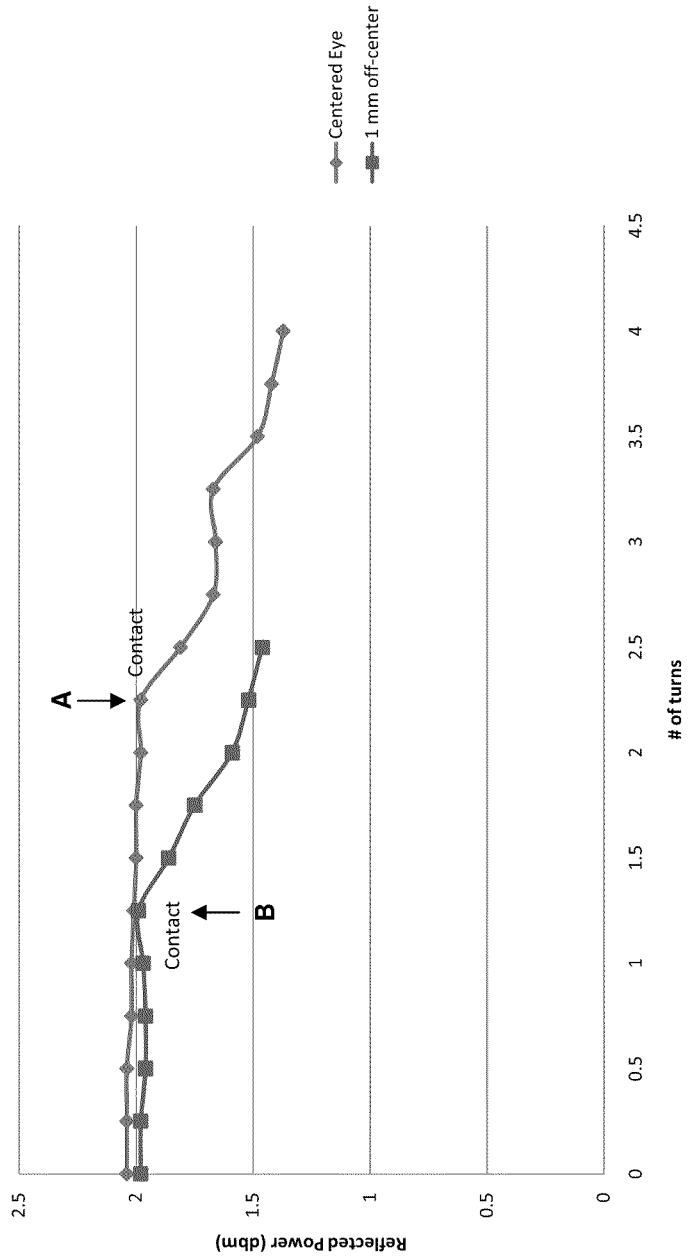
FIG. 4 illustrates an example graph of reflected power as a function of the position of the energy conducting element relative to the eye when the energy conducting element is positioned according to aspects of the present invention.

To demonstrate the sensitivity of the system to tissue contact, experiments were conducted with the system 200 to yield the graph of FIG. 4, which shows reflected power as a function of the position of the energy conducting element relative to the eye. In particular, the x-axis represents the number of turns that lowers the energy conducting element 111 along screw-like threads into position over the eye 1. The number of turns increases until the energy conducting element 111 moves into greater contact with the eye 1. The y-axis is a measure of reflected power in units of dBm (power ratio in decibels (dB) of the measured power referenced to one milliwatt (mW)). As discussed previously, a lower reflected power indicates better contact with the eye 1. In these experiments, the energy conducting element 111, as shown in FIG. 3, included outer and inner electrodes with a thin interposing membrane, i.e., polyurethane with 50 micron thickness, providing a contact surface 111G with the eye. As shown in FIG. 4, one curve represents the reflected power for an energy conducting element 111 that is centered over the eye, while the other curve represents the reflected power for an energy conducting element 111 that is 1 mm from the centered position. As the applicator 110 was initially and slowly lowered toward the eye 1, the curves generally showed no change, remaining at approximately 2 dBm. The points A and B shown on the graph indicate where contact was achieved for the centered energy conducting element 111 and off-center energy conducting element 111, respectively. From the points A and B, contact with the eye increased as the number of turns increased. In other words, the energy conducting element 111 was lowered into position to applanate onto the eye 1. As movement of the energy conducting element 111 caused further applanation, the corresponding reflected power decreased. Accordingly, the results shown in FIG. 4 demonstrate that the reflected power can be measured to determine whether sufficient contact between the energy conducting element 111 and the eye 1 has been achieved to enable the desired transfer of energy to the eye 1. In operation, the reflected power may be measured as the energy conducting element 111 is moved into further contact with the eye 1, and the decrease in the reflected power corresponding to the increase in contact may be monitored to determine when the desired amount of applanation has been achieved.

Although the embodiments described above involve systems in which the reflected power decreases as the amount of contact increases, the reflected power in other embodiments increases as the amount of contact increases. It is to be understood that the tuning or calibration of the system determines whether the reflected power decreases or increases as the amount of contact increases. In general, a change in the amount of contact between the applicator and the eye is indicated by a change in the reflected power.

As described previously, coolant pulses may also be applied to the eye to preserve the epithelium or surface of the eye during thermal treatment with microwaves. For example, a pulse train with 5 ms ON and 5 ms OFF may be utilized and repeated 3-20 times. Monitoring the effect of the coolant pulses is important, because the coolant application helps to protect the surface of the eye as described previously. Ordinary flow meters, however, may not be sufficiently able to detect and monitor short pulses of coolant on the order of approximately 5 ms to 50 ms as such pulses generally deliver small volumes of coolant, e.g., on the order of microliters. To solve this problem, further aspects of the present invention are able to detect coolant pulses by measuring their effect on the measured forward and reflected power as delivered to the eye. For example, the system 200 shown in FIG. 3 includes a dual directional coupler 122 that may be employed to sample the microwaves and determine the forward power and the reflected power to provide outputs 123 and 124, respectively. In another embodiment, a temperature sensor may be used to detect coolant pulses.

Figure 5:
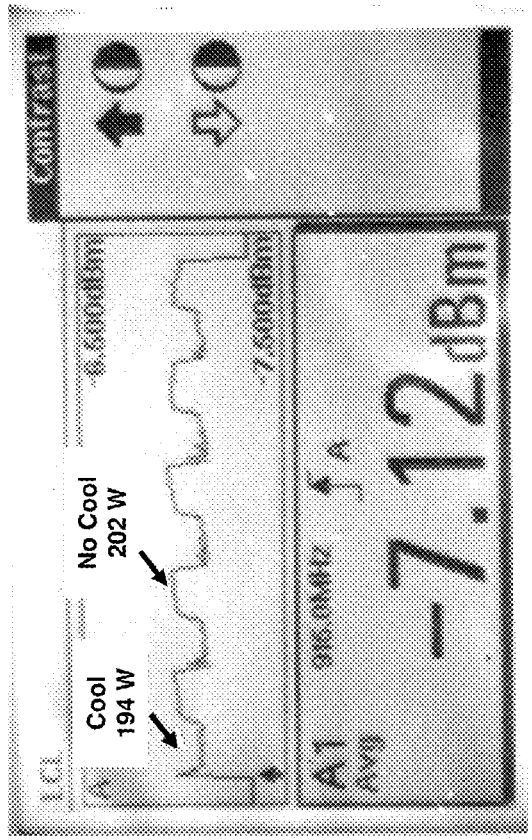
FIG. 5 illustrates an example graph of forward power as a function of time, showing how forward power changes when coolant pulses are delivered according to aspects of the present invention.

Detecting coolant pulses according to power measurements is sufficiently precise to identify a pulse train, even if, for example, it includes short 10 ms pulses. FIG. 5 illustrates an example graph of forward power as a function of time, which shows how forward power changes when coolant pulses are delivered. FIG. 5 illustrates five pulses of cooling and five no-cooling periods with microwave power as a single long pulse over the entire period. When the coolant is delivered in a 10 ms pulse, for example, the forward power decreases to approximately 194 W. During the period between pulses when no coolant is delivered, the forward power increases to approximately to 202 W. As explained above, it is to be understood that the calibration or tuning of the system determines whether the reflected power increases or decreases.

Figure 6:
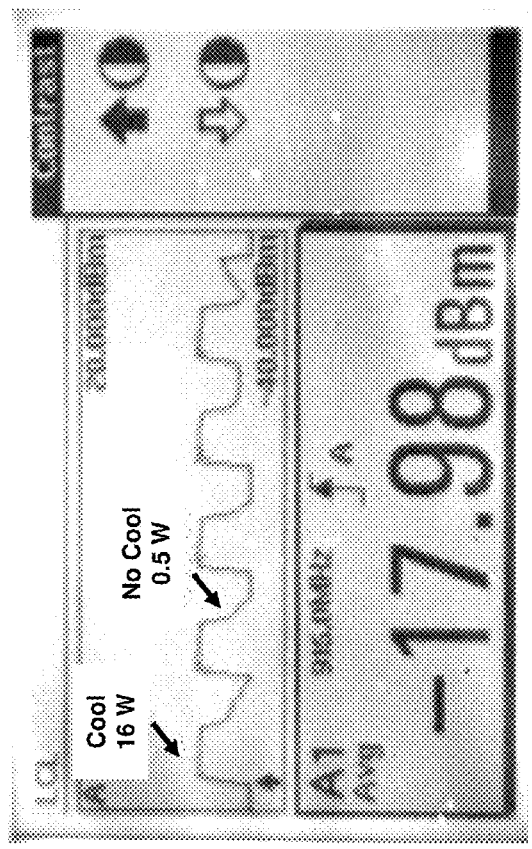
FIG. 6 illustrates an example graph of reflected power as a function of time, corresponding to the results illustrated in FIG. 5, showing how reflected power changes when coolant pulses are delivered according to aspects of the present invention.

Correspondingly, FIG. 6 illustrates an example graph of reflected power as a function of time for the same pulse train, which shows how reflected power changes when coolant pulses are delivered. When the coolant is delivered in a 10 ms pulse, for example, the reflected power increases to 16 W. In between pulses, the power drops to 0.5 W. Thus, monitoring the forward and/or reflected power over time provides a non-invasive means of monitoring the application of cooling pulses applied to the eye.

Referring to FIG. 6, the peaks in the curves resulting from the application of coolant that are not generally square, indicating the presence of a warm-up period between coolant applications. The shape of the curve indicates the amount of coolant applied and the amount of rewarming between applications of coolant.

Long cooling pulses may also be detected by monitoring the forward and/or reflected power. For example, if a 50-100 ms pulse of microwaves is applied, the system may detect a cooling pulse is applied for the whole microwave pulse duration or any part thereof.

FIG. 7A illustrates a block diagram of a tuning element 150. The tuning element 150 includes conductive components incorporating at least one adjustable aspect such that a modification of the adjustable aspect results in a change in either the inductance, or the capacitance, or both of an electrical circuit connected to the tuning element 150. By modifying either the inductance, or capacitance, or both of an electrical circuit according to adjustments to the at least one adjustable aspect, the tuning element 150 enables the circuit to be tuned to a particular impedance value by making changes to the at least one adjustable aspect of the tuning element 150.

The tuning element 150 may include an inner conductor 150B and an outer conductor 150A electrically connected to a short connector 150E. In an embodiment, the adjustable aspect may be embodied as a short connector 150E that may be adjustably electrically connected between the inner conductor 150B and the outer conductor 150A. The short connector 150E may be mechanically manipulated so as to move along a path substantially between the outer conductor 150A and the inner conductor 150B. While the short connector 150E moves along the path between the outer conductor 150A and the inner conductor 150B it may maintain a continuous electrical connection between the outer conductor 150A and the inner conductor 150B or it may establish only an intermittent electrical connection between the outer conductor 150A and the inner conductor 150B. Alternatively, the short connector 150E may establish no electrical connection at all between the outer conductor 150A and the inner conductor 150B while moving along a path enclosed by the outer conductor 150A and the inner conductor 150B only to effect an electrical connection between the outer conductor 150A and the inner conductor 150B once mechanical manipulation of the short connector 150E is halted. In an alternative embodiment, the short connector 150E may be embodied as an elastic or deformable conductive material which has an electrical connection on the outer conductor 150A that is fixed in position, and which is connected to the inner conductor 150B with a connection that may be adjusted in position. Alternatively, open stubs of varying lengths may be used in the place of or in addition to shorted stubs.

Figure 15:
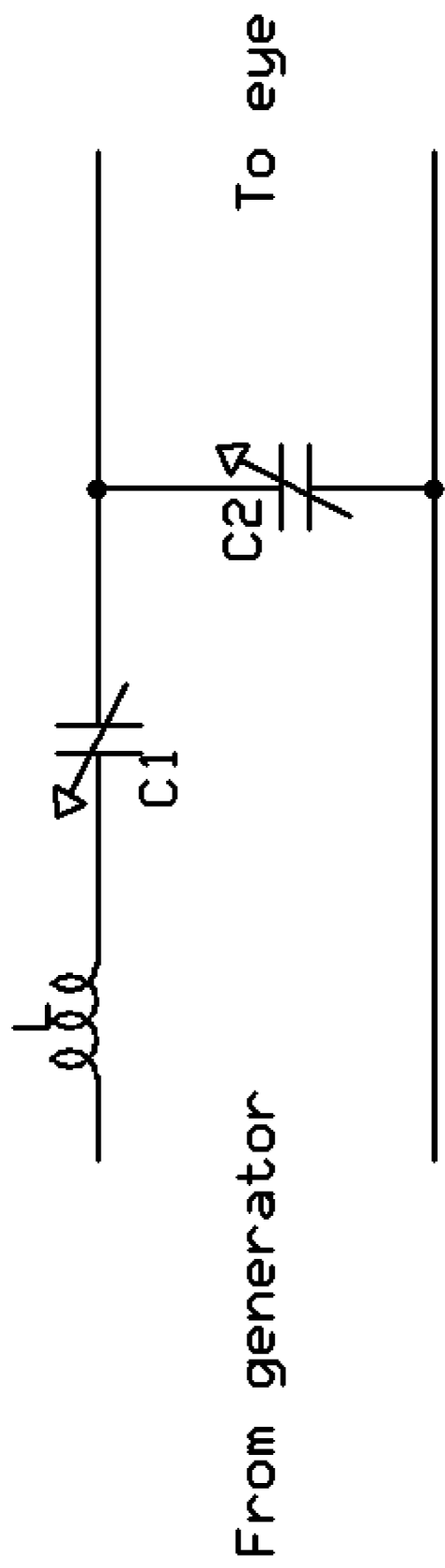
FIG. 15 illustrates an example circuit with adjustable parameters that may be used for tuning purposes in lieu of or in addition to the fixed single or double tuning stub herein described according to aspects of the present invention.

In general, any circuit with adjustable parameters that change the inductance and/or capacitance of the system may be used for tuning purposes in lieu of or in addition to the fixed single or double tuning stub herein described. An example of such a circuit is shown in FIG. 15. In the embodiment where the double tuning stubs are replaced by such a circuit, it is contemplated that the software-controlled tuning adjustments can be made with motorized variable capacitors, a binary capacitor cascade and solid state switches, and the like.

The short connector 150E, the inner conductor 150B, and the outer conductor 150A are each composed, at least in part, of suitable electrically conducting materials. The inner conductor 150B, the outer conductor 150A, and the short connector 150E may be formed, for example, of aluminum, stainless steel, brass, copper, silver, other metals, metal-coated plastic, or any other suitable conductive material. The materials used to construct the inner conductor 150B and the outer conductor 150A may be chosen, for example, in order to effect a characteristic impedance value for an electrical circuit connected to the outer conductor 150A and the inner conductor 150B. The dimensions of the outer conductor 150A and the inner conductor 150B may also be chosen in order to effect a characteristic impedance value for an electrical circuit connected to the outer conductor 150A and the inner conductor 150B. For example, when the tuning element 150 is embodied as having substantial cylindrical symmetry such that both the outer conductor 150A and the inner conductor 150B are embodied as cylinders about a common axis of symmetry, adjustments to the diameters of the inner conductor 150B and the outer conductor 150A may be used to adjust the impedance of the tuning element 150. In an example embodiment the impedance of the tuning element 150 may be adjusted to be 50 Ohms (50Ω).

The tuning element 150 further includes an electric motor 150F which is mechanically engaged to the short connector 150E via a mechanical connection 150G. The mechanical connection 150G may incorporate belts, cogs, wheels, pulleys, screws, levers, devices applying torque, or any other conventional means of achieving movement of the short connector 150G. In an embodiment, the operation of the electric motor 150F is mediated by automated computer control, which may be achieved using the controller 140.

In operation of an embodiment of the tuning element 150 the controller 140 may send a command to the electric motor 150F to move the short connector. The command may be sent and received via an electrical connection or via a wireless signal or any other conventional method of sending digital or analog information across distances. The electric motor 150F may then engage the mechanical connection 150G to move the short connector 150E along a path substantially enclosed by the outer conductor 150A and the inner conductor 150B.

FIG. 7B illustrates a perspective view of an embodiment of a tuning element 150, which shows a cut-away sectional view. As shown in FIG. 7B the tuning element 150 terminates at a proximal end 150H. In the embodiment illustrated in FIG. 7B, the inner conductor 150B may define a cylinder, which may be either solid or hollow, while the outer conductor. In the embodiment illustrated in FIG. 7B the area between the inner conductor 150B and the outer conductor 150A creates an annular gap 150C. The annular gap 150C may be embodied as an empty space, or it may be filled with a suitable dielectric material, which may be used, at least, to achieve a substantially constant spacing between the inner conductor 150B and the outer conductor 150A. Additionally, in an embodiment where the annular gap 150C is filled with a dielectric material, the dielectric material may be chosen in order to effect a desired impedance of a circuit containing the inner conductor 150B and the outer conductor 150A. When the inner conductor 150B and the outer conductor 150A are both constructed to have cylindrical symmetry about a central axis, then the annular gap 150C has cylindrical symmetry about the same axis.

Further illustrated in FIG. 7B is a short connector 150E, which provides an electrical connection between the inner conductor 150B and the outer conductor 150A. In an example embodiment, the short connector 150E may be configured so as to move in a direction parallel to the axis of cylindrical symmetry of the inner conductor 150B and outer conductor 150A, with one such direction indicated by the arrow in FIG. 7B. The region of the tuning element 150 between the proximal end 150H and the point of connection between the inner conductor 150B and the short connector 150E defines the length of a waveguide that is open on the proximal end 150H. Thus, an example embodiment of the tuning element 150 is a system for incorporating a waveguide of adjustable length into a circuit including the inner conductor 150B and the outer conductor 150A, wherein the length of the waveguide is adjustable upon command of the controller 140 that may cause the electric motor 150F to engage the mechanical connection 150G to mechanically manipulate the short connector 150E and thereby effect a change in the length of the waveguide between the proximal end 150H and the point of intersection between the inner conductor 150B and the short connector 150E. In the example embodiment shown in FIG. 7B the short connector 150E is depicted capable of moving in a direction transverse to its dominant length, but the short connector 150 may be oriented in any manner while it is mechanically manipulated so as to effect a change in length of the waveguide located between the proximal end 150H and the point of intersection between the inner conductor 150B and the short connector 150E.

FIG. 7C illustrates a side view cross section of an embodiment of a tuning element 150. The embodiment of the tuning element 150 includes an inner conductor 150B, an outer conductor 150A, a short connector 150E which may be mechanically manipulated in a direction substantially parallel to the axis of symmetry of the inner conductor 150B and the outer conductor 150A, as shown by the arrows in the FIG. 7C. FIG. 4C further illustrates a proximal end 150H such that the distance between the proximal end 150H and the point of intersection between the inner conductor 150B and the short connector 150E is defined by The example embodiments of the tuning element 150 shown in FIGS. 7A, 7B, and 7C are shown for example purposes only. The tuning element 150 includes conductive components incorporating at least one adjustable aspect such that a modification of the adjustable aspect results in a change in either the inductance, or the capacitance, or both of an electrical circuit in connection with the tuning element 150. By modifying either the inductance, or capacitance, or both of an electrical circuit according to adjustments to the at least one adjustable aspect, the tuning element 150 enables the circuit to be tuned to a particular impedance value by making changes to the at least one adjustable aspect of the tuning element 150.

Furthermore, although the tuning element 150 is shown and described in one embodiment in FIGS. 7A, 7B, and 7C, it is contemplated that the tuning element 150 is not required for use in all embodiments of the invention. For example, in another embodiment of the eye therapy system, the applicator can be carefully tuned to an eye once, and will not have to be tuned again for subsequent uses.

Figure 8:
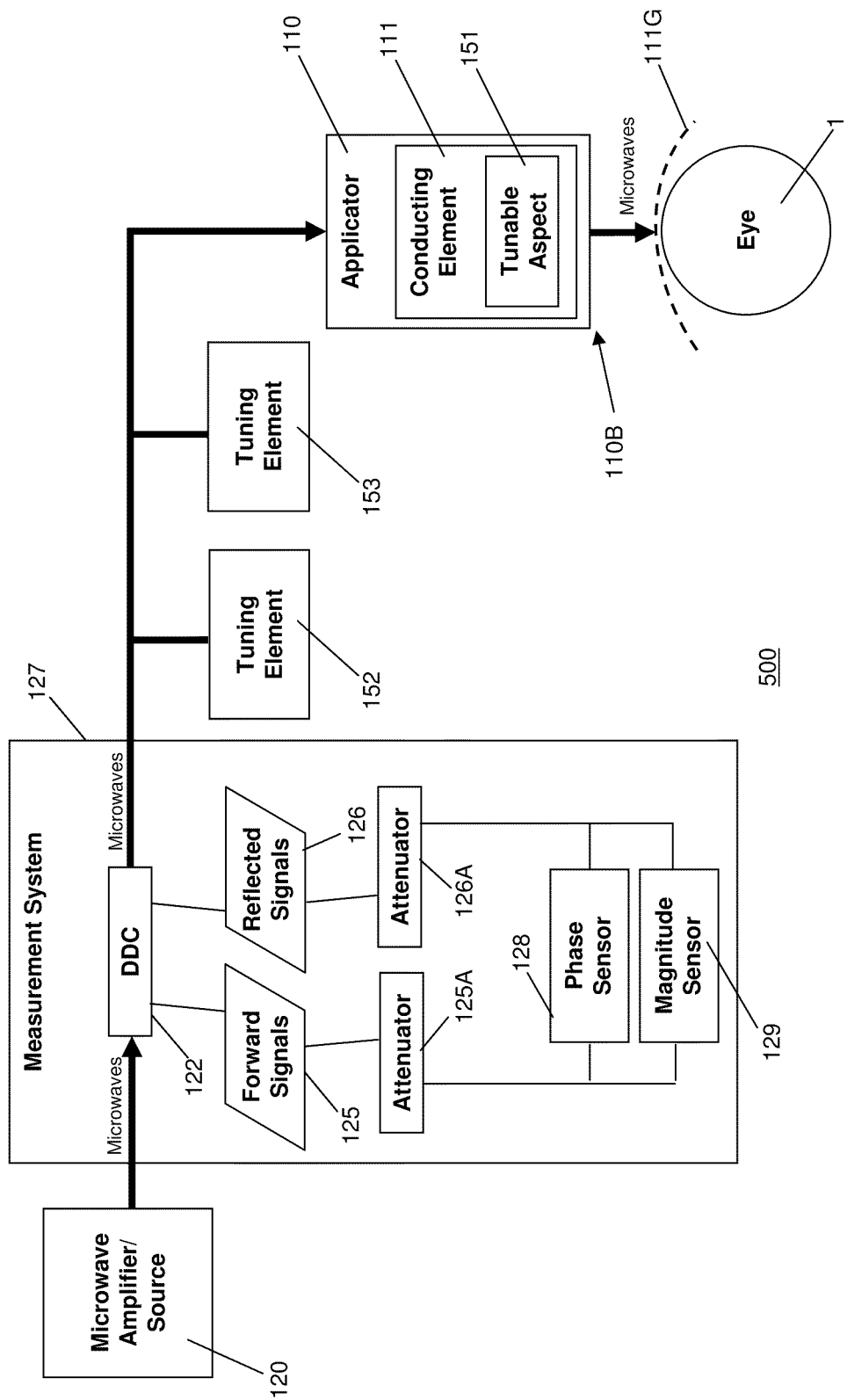
FIG. 8 illustrates an example configuration for a system for measuring an electrical characteristic of an eye according to aspects of the present invention.

FIG. 8 illustrates a system 500 for measuring an electrical characteristic of an eye 1. An embodiment of the system 500 may utilize a measurement system 127 to measure aspects of a reflection coefficient. The reflection coefficient is the reflected voltage divided by the forward voltage, where the voltage is a complex number that is a function of magnitude and phase. An example embodiment of the measurement system 127 may incorporate a phase sensor 128 or a magnitude sensor or both and includes a dual directional coupler (DDC) 122, which provides outputs to split signals into forward signals 127 and reflected signals 126. In an example embodiment depicted in FIG. 5 the forward signal output 125 of the DDC 122 may be electrically connected to an attenuator 125A, and the output of the attenuator 125A may then be electrically connected to a phase sensor 128, a magnitude sensor 129, or to both. Additionally, the reflected signal output 126 may be electrically connected to an attenuator 126A, and the output of the attenuator 126A may then be electrically connected to a phase sensor 128, a magnitude sensor 129, or to both. An embodiment of the system 500 may also include a plurality of tuning elements. For example, the embodiment of the system 500 depicted in FIG. 8 includes a first tuning element 152 and a second tuning element 153 connected in parallel to the output of the measurement system 127 at predetermined locations.

The tuning elements 152 and 153 may each include conductive components incorporating at least one adjustable aspect such that a modification of the adjustable aspect results in a change in either the inductance, or the capacitance, or both of an electrical circuit in connection with the tuning elements 152 and 153. By modifying either the inductance, or capacitance, or both of the electrical circuit according to adjustments to the at least one adjustable aspect, the tuning elements 152 and 153 enables the circuit to be tuned to a particular impedance value by making changes to the at least one adjustable aspect of the tuning elements 152 and 153. The tuning elements 152 and 153 may substantially incorporate many of the features of the tuning element 150 described above and illustrated in FIGS. 7A, 7B, 7C.

An embodiment of the system 500 for measuring an electrical characteristic of an eye 1 may incorporate an energy source 120, which may include an oscillator for generating energy at microwave frequencies and an output which is electrically connected to an input of the DDC 122. An output of the DDC 122 may then be connected to an applicator 110. The applicator 110 may include a conducting element 111 for application of energy at its proximal end 110B to an eye 1 at a contact surface 111G. Aspects of the applicator 110 may incorporate features of the applicator 110 shown in FIG. 1. The conducting element may include a tunable aspect 151. The tunable aspect 151 may be embodied as an adjustable conducting element between the outer conductor 110A and the inner conductor 110B so as to adjust the output impedance of the applicator 110. The measurement system 127 is electrically connected between the energy source 120 and the applicator 110. Between the measurement system 127 and the applicator 110 a plurality of tuning elements connected in parallel at predetermined locations. For example a first tuning element 152 and a second tuning element 153 may be connected in parallel between the measurement system 127 and the applicator 110.

In operation of the system 500 for measuring an electrical characteristic of an eye 1, energy may be generated in the energy source 120 at a microwave frequency. The microwaves may then be conducted to an applicator 110 after passing through a measurement system 127, which incorporates a DDC 122 and a phase sensor 128 or a magnitude sensor 129 or both. Upon conduction of the microwave energy to the eye 1 through the contact surface 111G, some microwave energy is transmitted into the eye 1, while some additional microwave energy is reflected at the junction to travel back through the conducting element 111 toward the measurement system 127. The sum of the microwave energy reflected, the microwave energy transmitted, and all the microwave energy lost due to line losses and radiation leaks will substantially equal the amount of microwave energy generated in the energy source 120. When the microwave energy passes through the DDC 122 from the energy source 120, a signal indicative of the amount of forward power is provided to the forward signal output 125. When the reflected microwave energy passes back through the DDC 122 upon reflection from the applicator 110, a signal indicative of the reflected signal is provided to the reflected signal output 126. The forward signal output 125 may then be passed through an attenuator 125A, which may reduce the amplitude of the forward microwave signal by a predetermined amount. Similarly, the reflected signal output 126 may then be passed through an attenuator 126A, which may reduce the amplitude of the reflected microwave signal by a predetermined amount. The reflected and forward microwave signals may then each be provided to either a phase sensor 128, or a magnitude sensor 129, or both in order to determine the amount of microwave energy reflected compared to the amount of microwave energy generated. As is conventionally understood, this information may also allow for the calculation of the impedance value of the eye 1 when the impedance value of the system 500 is known. Although, in an example embodiment it is not necessary to know the impedance of the system 500 in order to achieve a desired difference in impedance between the eye 1 and the system 500.

In an example embodiment, adjusting the impedance of the applicator 110 may be advantageous, for example, in order to achieve a desired efficiency of energy absorption to the eye 1 by the applicator 110. As is conventionally known, when energy is conducted or transmitted across a surface boundary, i.e. across a junction wherein a first portion of the junction has a first impedance value and a second portion of the junction has a different impedance value, some energy is transmitted through the junction and some is reflected. Energy is most efficiently transmitted when the two impedances are as near as possible to identical. Thus an applicator 110 which includes a tunable aspect 151 in the conducting element 111 so as to adjust the impedance value of the applicator 110 may allow for adjustment of the impedance of value of the applicator 110 so as to correspond in a desirable manner with the impedance value of the eye 1.

In an alternative embodiment, the tunable aspect 151 and/or the first tuning element 152 and/or the second tuning element 153 may not include an adjustable conducting element between the outer conductor 110A and the inner conductor 110B, but may be embodied as a conducting element providing an electrical connection between the outer conductor 110A and the inner conductor 110B which may be fixed in place in a removable or permanent manner so as to allow for the placement of the tunable aspect 151 and/or the first tuning element 152 and/or the second tuning element 153 to be determined according to an electrical characteristic of the system 500.

Figure 9:
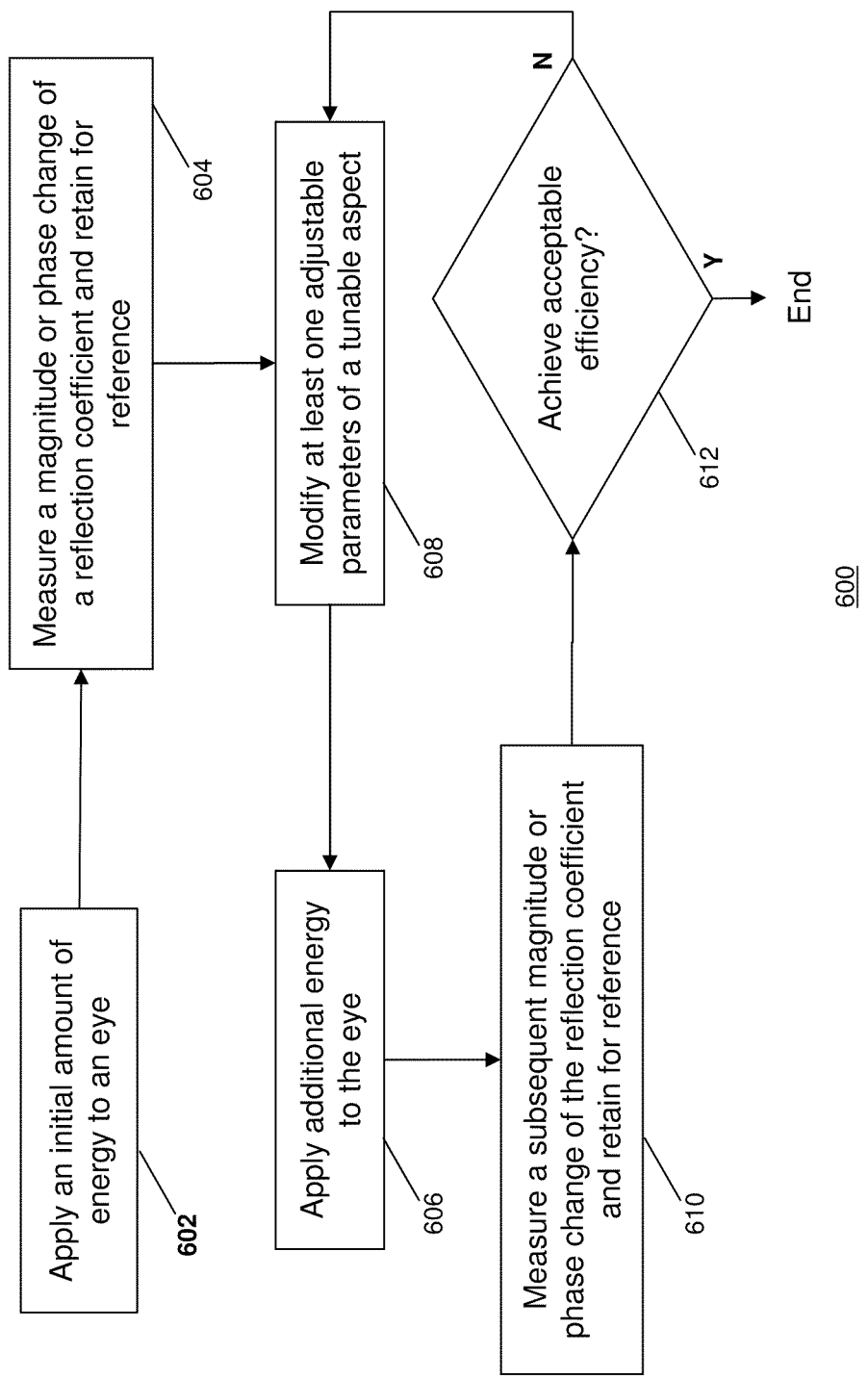
FIG. 9 illustrates a flowchart showing an example of a method of adjusting a tunable aspect of the applicator according to aspects of the present invention.

FIG. 9 illustrates a flowchart showing an example of a method 600 of adjusting a tunable aspect 151 of the applicator 110 so as to achieve a desired transmission efficiency between the conducting element 111 and the eye 1. In an example embodiment, the method 600 of adjusting a tunable aspect 151 may be exercised using, for example, a system 500 for measuring an electrical characteristic of an eye 1. An embodiment of the method 600 of adjusting a tunable aspect 151 includes a first step 602 where a first amount of energy is applied to the eye 1. The method 600 may further include a second step 604 wherein a measurement of a magnitude of phase change of a reflection coefficient may be measured and then retained for reference. The measurement accomplished in the second step 604 may be accomplished with a measurement system 127, such as that described in the system 500 appearing in FIG. 8. The method 600 may further include a third step 608 where at least one adjustable parameter of a tunable aspect 151 may be adjusted. In an example embodiment utilizing the system 500 for measuring an electrical characteristic of an eye 1, the third step 608 may adjust the impedance value of the system 500. The method 600 may further include a fourth step 606 wherein an additional amount of energy is applied to the eye 1. The method 600 may further include a fifth step 610 wherein a subsequent magnitude or phase change of the reflection coefficient is measured and retained for reference. The method 600 may further include a sixth step 612 wherein a determination is made as to whether an acceptable efficiency has been achieved. If it is determined in the sixth step 612 that an acceptable efficiency has been achieved then the method 600 ends. If, on the other hand, it is determined in step six 612 that an acceptable efficiency has not been achieved, then at least one parameter of the tunable aspect may be modified again in the third step 608.

In operation, the operation of the first step 602 enables the measurement activity accomplished in the second step 604. Upon completion of the second step 604, the third step 608 is undertaken, which is followed by steps four 606 and five 610, which are accomplished in a manner substantially similar to the completion of steps one 602 and two 604. Following step five 610, step six 612 is undertaken and depending on the determination made in step six 612, steps three through six, 608, 606, 610, and 612 may be completed in a loop until a determination is made in step six 612 that an acceptable efficiency has been attained so as to end the method 600.

Figure 12:
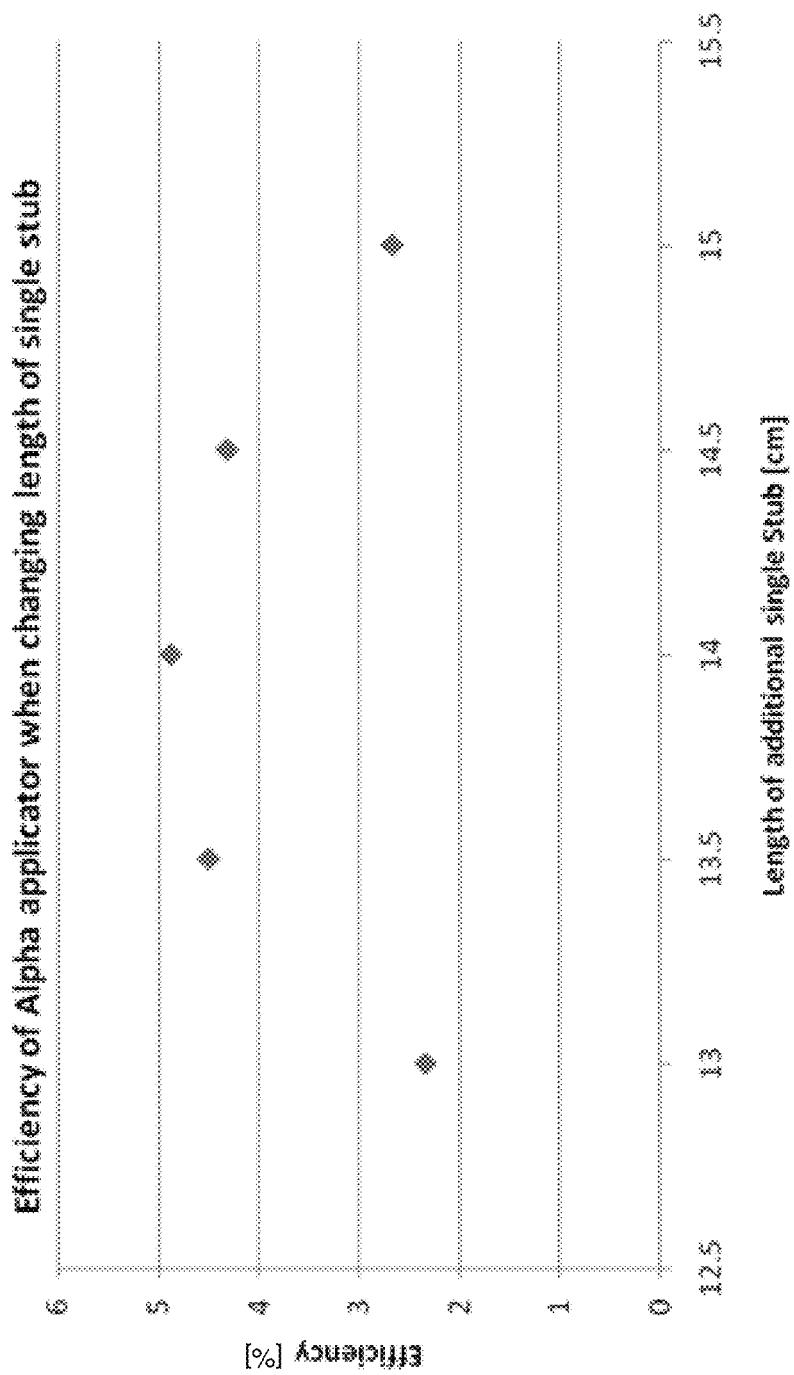
FIG. 12 illustrates an example graph of the efficiency of an applicator when changing the length of a single tuning stub according to aspects of the present invention.

In an example embodiment, the determination in step six 612 may be based on achieving a predetermined minimal impedance mismatch, which may be determined after sampling a range of values until a local or global minimum is identified in a value of a reflection coefficient as measured in the measurement system 127, as shown, for example, in FIG. 8. Estimating the location substantially equivalent to the local or global minimum value of the reflection coefficient with respect to the tunable aspect 151 may be accomplished by comparing all of the collected values stored in operation of the iterative method 600, or it may be based on a subset of those values. The determination may be made using a software program to fit a predetermined mathematical function to a curve of measured values of the reflection coefficient, such as the curve represented in FIG. 12. As shown, FIG. 12 illustrates the efficiency of an applicator as a function of the length of a single stub. The efficiency shown is the difference between forward power and reflected power, divided by forward power. This efficiency represents the percentage of energy leaving the applicator that is successfully transmitted into the eye.

In another example embodiment of the method 600, the determination in step six 612 may be based on achieving an acceptable impedance mismatch. That is, the efficiency may be deemed acceptably efficient so as to end the method 600 when the measurement system 127 measures an effective impedance mismatch below some predetermined threshold value. In another example embodiment of the method 600, the determination in step six 612 may be deemed acceptably efficient so as to end the method 600 when the measurement system 127 measures an effective impedance within a certain threshold of upper and lower boundaries. Alternatively, an embodiment of the method 600 may incorporate a determination in step six 612 that is some combination of each of these.

Figure 10:
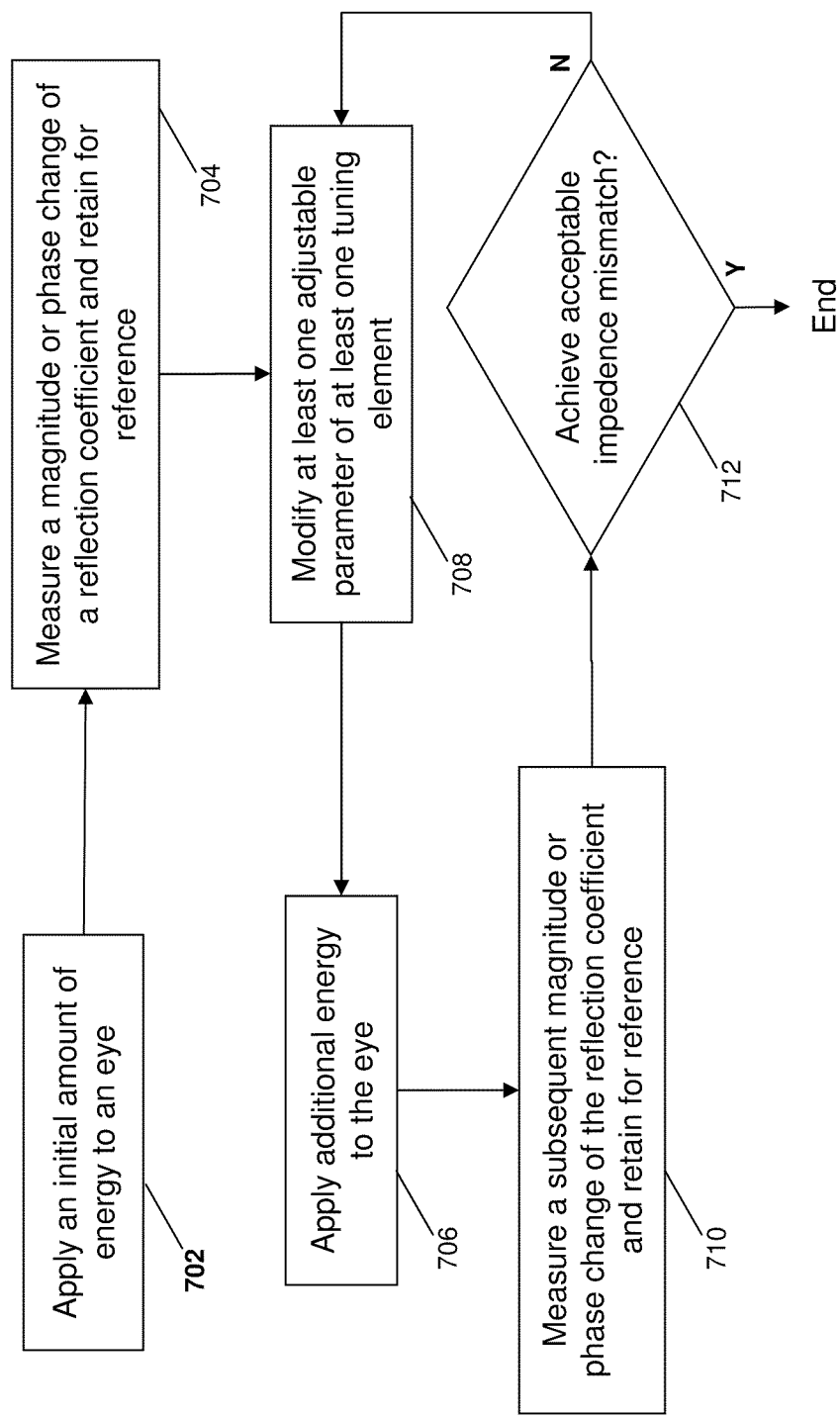
FIG. 10 illustrates a flowchart showing an example of a method of adjusting at least one tuning element according to aspects of the present invention.

FIG. 10 illustrates a flowchart showing an example of a method 700 of adjusting at least one tuning element so as to achieve an acceptable impedance mismatch. In an example embodiment, the method 700 of adjusting at least one tuning element may be exercised using, for example, a system 500 for measuring an electrical characteristic of an eye 1 and the at least one tuning element may be a first tuning element 152 or a plurality of tuning elements, such as the first tuning element 152 and second tuning element 153 shown in FIG. 8 connected in parallel in the system 500. An embodiment of the method 700 of adjusting at least one tuning element includes a step one 702 where a first amount of energy is applied to the eye 1. The method 700 may further include a step two 704 wherein a measurement of a magnitude of phase change of a reflection coefficient may be measured and then retained for reference. The measurement accomplished in step two 704 may be accomplished, for example, with a measurement system 127, such as that described in the system 500 appearing in FIG. 8. The method 700 may further include a step three 708 where an adjustable parameter of at least one tuning element may be adjusted. In an example embodiment utilizing the system 500 for measuring an electrical characteristic of an eye 1, the third step 708 may adjust the impedance value of the system 500 by adjusting at least one adjustable parameters of at least one tuning element such as the tuning elements 152 and 153. The method 700 may further include a step four 706 wherein an additional amount of energy is applied to the eye 1. The method 700 may further include a step five 710 wherein a subsequent magnitude or phase change of the reflection coefficient is measured and retained for reference. The method 700 may further include a step six 712 wherein a determination is made as to whether an acceptable impedance mismatch has been achieved. If it is determined in step six 712 that an acceptable efficiency has been achieved, then the method 700 ends. If, on the other hand, it is determined in step six 712 that an acceptable efficiency has not been achieved, then at least one parameter of the tunable aspect may be modified again by retuning to step three 708.

In operation, the operation of the first step 702 enables the measurement activity accomplished in the second step 704. Upon completion of the second step 704, the third step 708 is undertaken, which is followed by steps four 706 and five 710, which are accomplished in a manner substantially similar to the completion of steps one 702 and two 704. Following step five 710, step six 712 is undertaken and depending on the determination made in step six 712, steps three through six, 708, 706, 710, and 712 may be completed in a loop until a determination is made in step six 712 that an acceptable impedance mismatch has been attained so as to end the method 700.

In another example embodiment of the method 700, the determination in step six 712 may be based on achieving an acceptable impedance mismatch. That is, the efficiency may be deemed acceptably efficient so as to end the method 700 when the measurement system 127 measures an effective impedance mismatch below some predetermined threshold value. When the determination in step six 712 is based on achieving an impedance mismatch of some threshold value, step five 710 may not retain subsequent values for future reference. In another example embodiment of the method 700, the determination in step six 712 may be deemed acceptably efficient so as to end the method 700 when the measurement system 127 measures an effective impedance within a certain threshold of upper and lower boundaries. Alternatively, an embodiment of the method 700 may incorporate a determination in step six 712 that is some combination of each of these.

Figure 11:
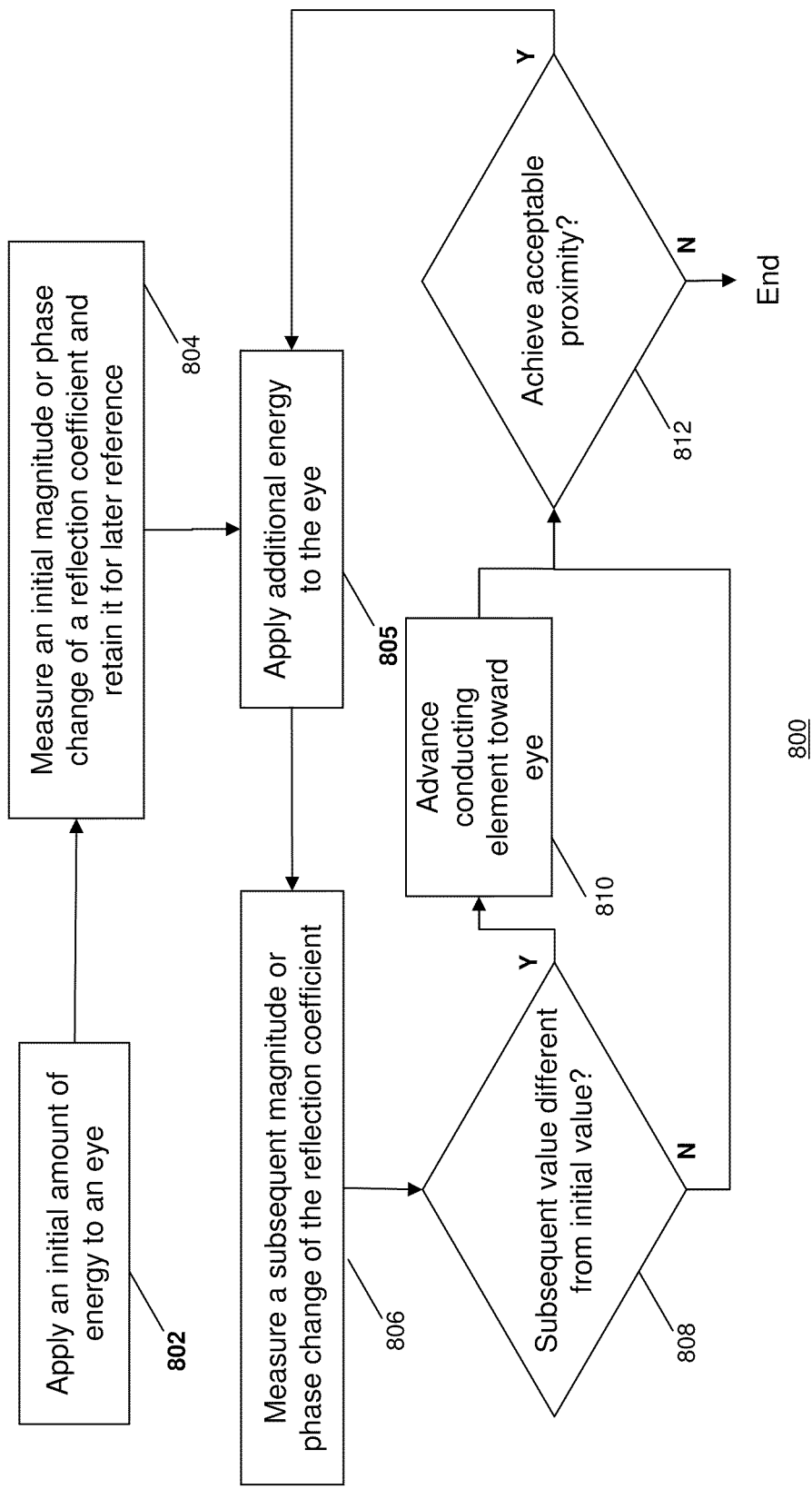
FIG. 11 illustrates an embodiment of a method for monitoring proximity of the energy conducting element to an eye according to aspects of the present invention.

FIG. 11 illustrates an embodiment of a method 800 for monitoring proximity of the conducting element 111 as previously described to an eye 1. The method 800 may be exercised, for example, utilizing a system 500 for measuring an electrical characteristic of an eye 1. The method 800 includes a step one 802, a step two 804, a step three 805, a step four 806, a step five 808, an optional step six 810, and a final step seven 812, which may provide for an iterative process to restart at step three 805. In an example embodiment of the method 800 for monitoring proximity to an eye 1, an initial amount of energy is applied to an eye 1 in step one 802. During the application of energy to an eye 1 started in step one 802, an initial magnitude or phase change of a reflection coefficient is measured and retained for later reference in step two 804. Following the completion of step two 804, an additional amount of energy is applied to the eye 1 in step three 805. The application of energy to the eye 1 in step three 805 allows for a subsequent measurement of a magnitude or phase change of the reflection coefficient in step four 806. In an example embodiment utilizing the system 500 for measuring an electrical characteristic of an eye 1, the measurement of the magnitude of phase change of a reflection coefficient in step two 804 and step four 806 may be accomplished using a measurement system 127. In step five 808 the subsequent value measured in step four 806 is compared with the initial value measured in step two 804. If the comparison in step five 808 determines that the subsequent value measured in step four 806 is different from the value measured in step two 804 then corrective measures may be taken in step six 810. The corrective measures taken in step six 810 in an embodiment utilizing the system 500 depicted in FIG. 8 may include, for example, an modification in the duration of the pulse length of an application of energy through the conducting element 111, an increase in the forward power generated in the energy source 120 so as to effect the transmission of a desired amount of microwave energy to the eye 1 for therapeutic treatment, and/or advancing the conducting element toward the eye. Alternatively, if the difference in the initial value measured in step 804 and the subsequent value measured in step four 806 are determined to exceed some predetermined threshold, then the method 800 may be terminated at step five 808 rather than advancing to step six 810 or step seven 812. If the determination in step 808 finds to difference between the initial value measured in step two 804 and the subsequent value measured in step four 806, then an additional determination is made in step seven 812. Following the corrective measures taken in step 810, an additional determination is made in step seven 812. The determination made in step seven 812 is whether to continue advancing the energy conducting element 111 toward the eye. Advancement may be halted if, for example, an individual using a system 500 for measuring electrical characteristics of an eye to apply energy to an eye indicates that advancement should be halted, for example, because acceptable proximity has been achieved. The determination to halt advancement may then be indicated by some savable means in communication with, for example, a controller 140, such that the information indicating advancement should be halted is retrievable by an automated process in step seven 812. If it is not discovered that advancement should be halted, then the method is restarted with step three 805. In an example embodiment, step seven 812 may provide for a predetermined rest time before restarting the method at step three 805 in order to achieve a desired duty cycle of applying corrections in step 810 and monitoring the proximity, which is principally accomplished in step five 808.

Figure 13:
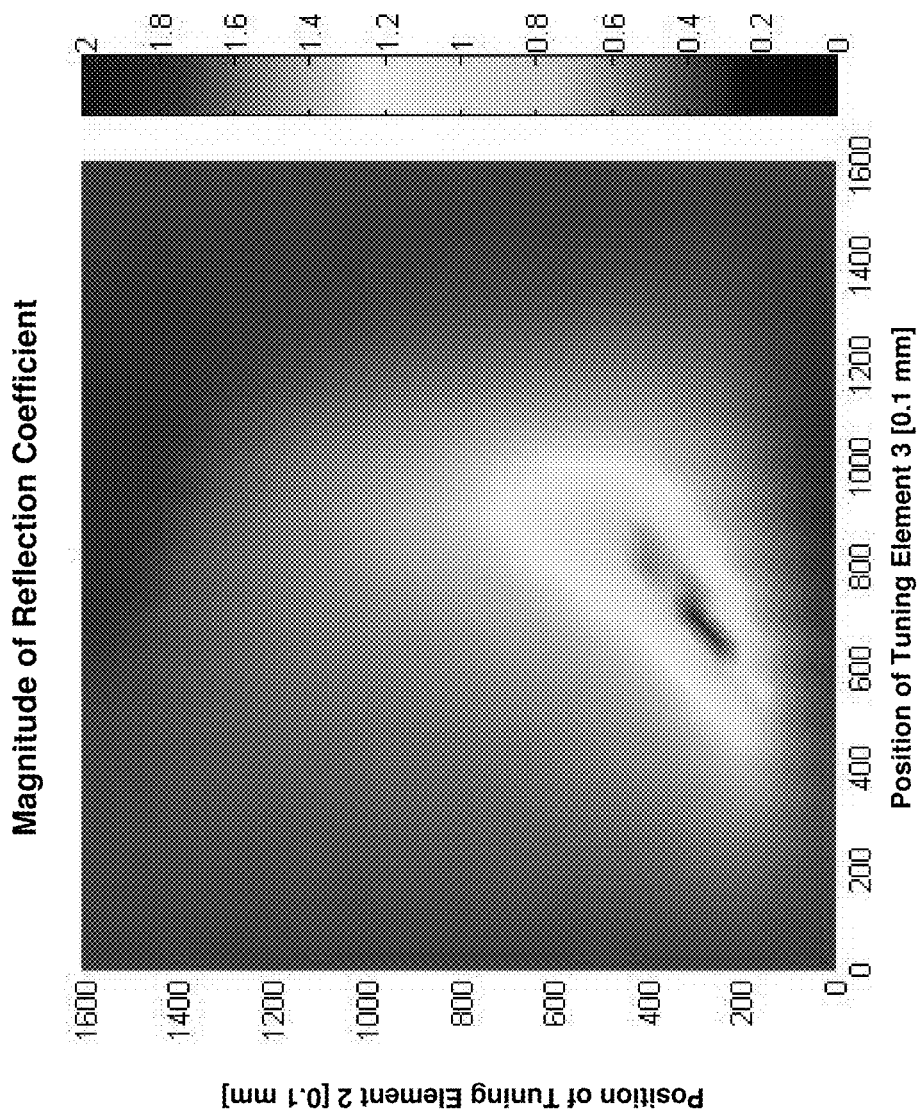
FIG. 13 illustrates an example graph of the reflected power for different positions of the tuning stubs according to aspects of the present invention.

FIG. 13 illustrates a plot of the magnitude of the reflection coefficient, |Γ|, against the positions of the short along the stubs of tuning element 2 and tuning element 3 from where they branch off from the main circuit. Location and depth of the minima depends on the geometry of the system 500 and on the contact of the microwave applicator 110 with the eye 1. In one embodiment, the method previously described with respect to FIG. 11 may be used to determine the minima or near-minima.

Figure 14:
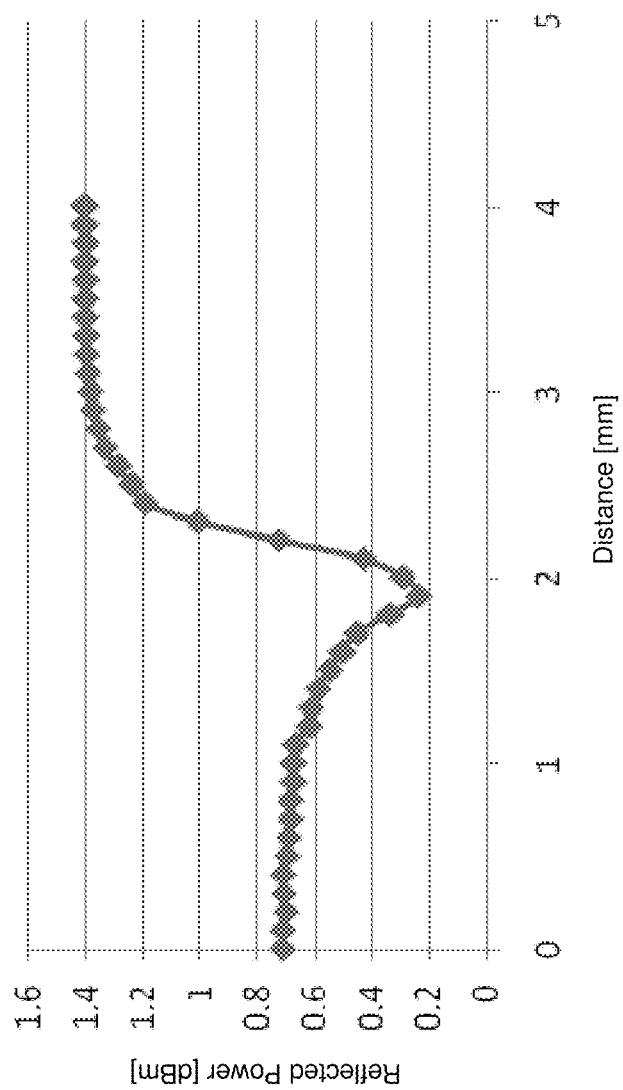
FIG. 14 illustrates an example graph of the reflected power as the electrodes advance towards the cornea according to aspects of the present invention.

FIG. 14 illustrates an example graph of the reflected power in dBm as the electrode 111B is positioned at various distances from corneal surface 2A. When the microwave applicator 110 equipped with movable electrode 111B is lowered onto the eye 1, the system 500 depicted in FIG. 8 can be used to sense proximity with the cornea. After the system 500 has been tuned to air or a similar reference, the electrode 111B are lowered towards the corneal surface 2A. As the electrode 111B approaches the corneal surface 2A, the reflected power changes from its original tuned to air value, as shown in FIG. 14. By monitoring the reflected power, the system can determine the correct location of the electrode 111B relative to the corneal surface 2A. Choosing a certain feature of the curve of FIG. 14 and stopping electrode movement once it is sensed ensures correct position of the electrode 111B independent of variations in eye geometry, and reproducible energy delivery.

The amount of impedance of the cornea may be determined according to patient characteristics, including, but not limited to, age, gender, corneal thickness, and other similar factors that affect how corneal changes may be induced. Data relating to such factors and corresponding impedances may be compiled from a sample of past patients and reduced to a nomogram, look-up table, or the like. This compiled data may then serve as a guide for determining the impedance in future treatments.

Figure 16:
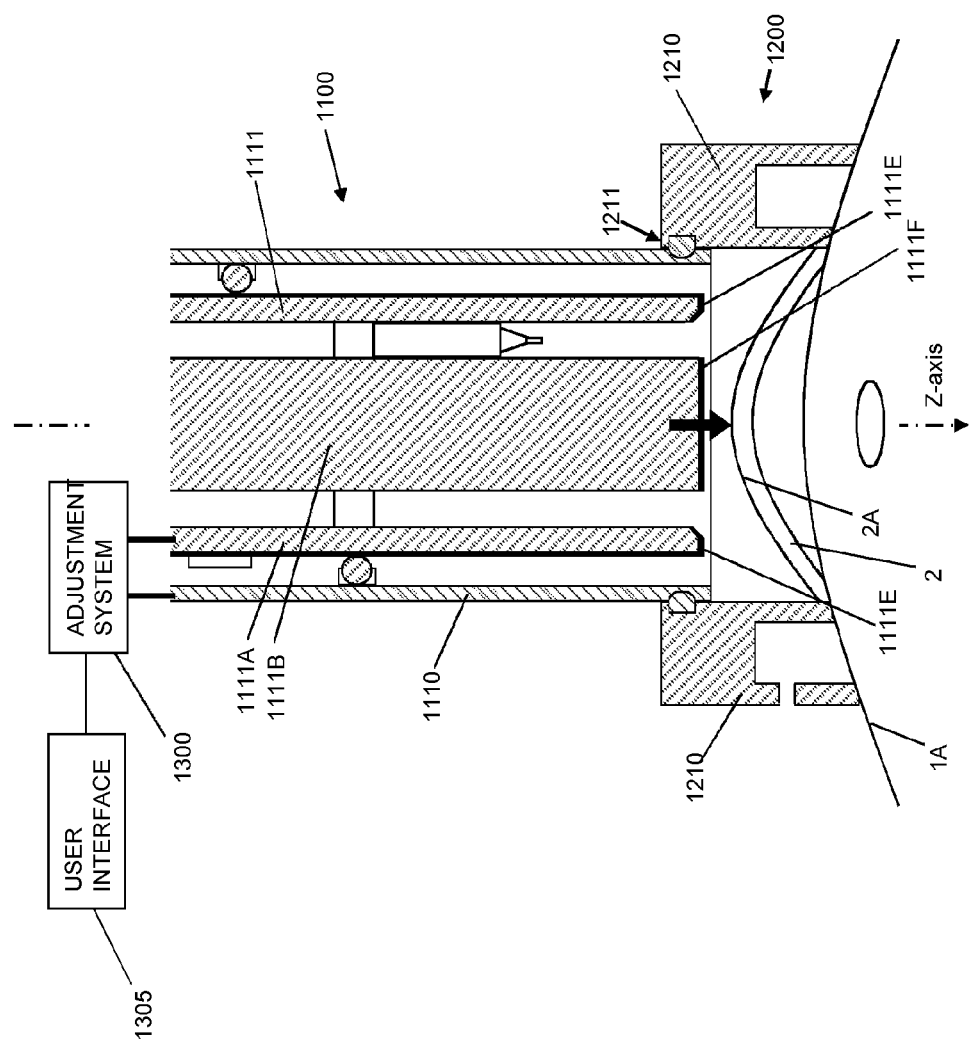
FIG. 16 illustrates a cross-sectional view of an automated adjustment system for adjustably coupling an energy conducting element to an applicator housing according to aspects of the present invention.

FIG. 16 illustrates an exemplary movement of an energy conducting element 1111 toward a cornea 2. Although adjusting the position of the energy conducting element 1111 may be achieved manually, a more automated adjustment system 1300, as shown in FIG. 16, can be employed. Advantageously, the adjustment system 1300 facilitates the accurate positioning of the energy conducting element 1111 against a corneal surface 2A. After an attachment element 1210 is fixed to the eye surface 1A, an applicator 1100 is guided into position within the passageway 1211 of the attachment element 1210, and the adjustment system 1300 can be easily operated to move the distal surfaces 1111E and 1111F of the energy conducting element 1111 against the corneal surface 2A.

The adjustment system 1300 may be further connected to a user interface system 1305 that accepts input from a user and correspondingly operates the adjustment system 1300. The user interface system 1305, for example, may be a device with a keypad to receive input from a user. The keypad may be part of a processing system, such as a conventional personal computer, with software to control the adjustment system 1300. Alternatively, the user interface system 1305 may be a device, such as a joystick, that receives instructions from the user through more mechanically oriented input.

In embodiments where the outer conductor 1111A and the inner conductor 1111B are fixedly coupled to each other, the adjustment system 1300 moves the outer conductor 1111A and the inner conductor 1111B as a single element relative to a housing 1110. However, in other embodiments, the outer conductor 1111A and the inner conductor 1111B may be decoupled so that they can be moved relative to each other. Accordingly, with the housing 1110 fixed relative to the eye 2 (e.g., with a positioning system 1200), the contact between the outer conductor 1111A and the corneal surface 2A may be controlled separately from the contact between the inner conductor 1111B and the corneal surface 2A.

Figure 17:
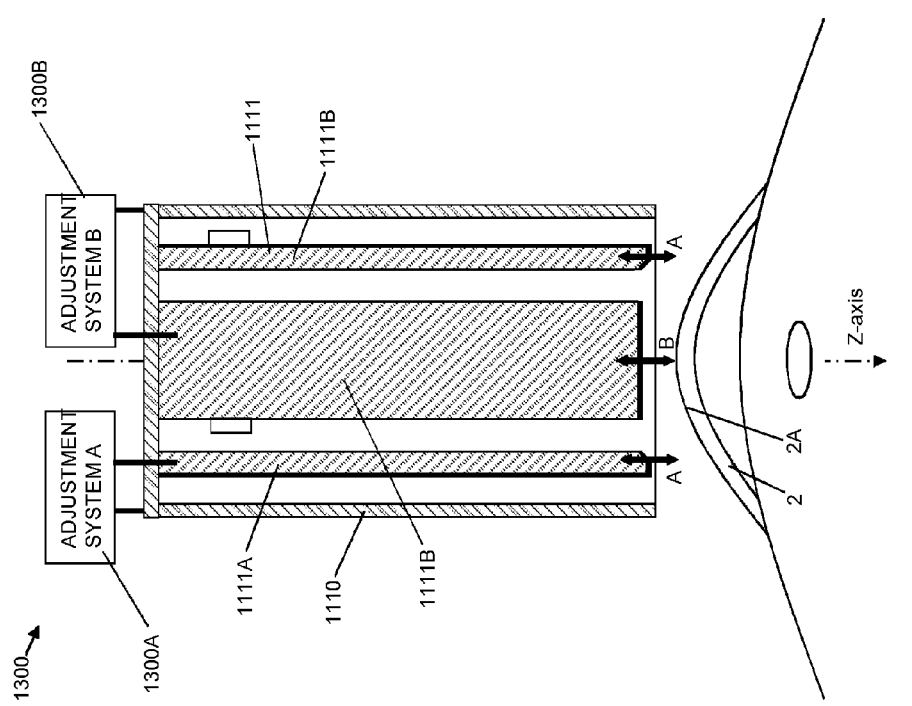
FIG. 17 illustrates a cross-sectional view of an embodiment that permits an outer electrode and an inner electrode according to aspects of the present invention to be moved relative to each other.

FIG. 17 illustrates an exemplary embodiment of the energy conducting element 1111 where the outer conductor 1111A follows a movement A and the inner conductor 1111B follows a movement B, where the movements A and B may be separately controlled. In particular, the energy conducting element 1111 may be employed with an adjustment system 1300A that moves the outer conductor 1111A relative to the housing 1110 and an adjustment system 1300B that moves the inner conductor 1111B relative to the housing 1110. Although the energy conducting element 1111 of FIG. 17 allows the movement A to be different from the movement B, the movement A can also be substantially similar to the movement B.

While the present invention has been described in connection with a number of exemplary embodiments, and implementations, the present inventions are not so limited, but rather cover various modifications, and equivalent arrangements. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A system for treating an eye disorder, comprising:
an energy source;
a thermokeratoplasty applicator configured to apply thermokeratoplasty therapy to an eye, the applicator having a distal end, the applicator being configured to receive an amount of energy from the energy source, a first portion of the energy received by the applicator configured to be transmitted through the distal end to the eye and a second portion of the energy received by the applicator being reflected from the distal end of the applicator;
a dual directional coupler configured to detect the reflected energy, the reflected energy being indicative of an amount of contact between the distal end and the eye, the dual directional coupler being further configured to provide a signal indicative of the detected reflected energy; and
an adjustment system configured to advance the distal end of the applicator toward the eye until a predetermined amount of contact is determined based on the signal indicative of the reflected energy,
wherein the signal corresponding to the reflected energy has a power that decreases as the amount of contact increases.

2. The system of claim 1, wherein the signal corresponding to the reflected energy has a power and the system further comprises a controller configured to determine whether the power is less than a threshold value.

3. The system of claim 1, wherein the amount of contact includes no contact.

4. The system of claim 1, wherein the applicator comprises:
a conducting element configured to conduct energy from the energy source to apply therapy to the eye; and
a covering configured to be removably attached to the conducting element, the covering having an interface surface configured to be positioned at the eye, at least a portion of the interface surface including one or more dielectric materials, the interface surface being configured such that the energy from the conducting element is deliverable to the eye through the interface surface.

5. The system of claim 4, wherein the covering forms an enclosure over a portion of the conducting element and the applicator further comprises a coolant delivery system, the coolant delivery system being configured to deliver coolant within the enclosure to cool the interface surface of the covering and the eye, and the enclosure being configured to prevent the coolant from directly contacting the eye.

6. The system of claim 1, wherein the energy supplied to the applicator is a microwave energy.

7. A system for treating an eye disorder, comprising:
an energy source;
a thermokeratoplasty applicator configured to apply thermokeratoplasty therapy to an eye, the applicator having a distal end, the applicator being configured to receive an amount of energy from the energy source, a first portion of the energy received by the applicator configured to be transmitted through the distal end to the eye and a second portion of the energy received by the applicator being reflected from the distal end of the applicator;
a dual directional coupler configured to detect the reflected energy, the reflected energy being indicative of an amount of contact between the distal end and the eye, the dual directional coupler being further configured to provide a signal indicative of the detected reflected energy; and
an adjustment system configured to advance the distal end of the applicator toward the eye until a predetermined amount of contact is determined based on the signal indicative of the reflected energy,
wherein the signal corresponding to the reflected energy has a power that increases as the amount of contact increases.

8. The system of claim 7, wherein the signal corresponding to the reflected energy has a power and the system further comprises a controller configured to determine whether the power is less than a threshold value.

9. The system of claim 7, wherein the amount of contact includes no contact.

10. The system of claim 7, wherein the applicator comprises:
a conducting element configured to conduct energy from the energy source to apply therapy to the eye; and
a covering configured to be removably attached to the conducting element, the covering having an interface surface configured to be positioned at the eye, at least a portion of the interface surface including one or more dielectric materials, the interface surface being configured such that the energy from the conducting element is deliverable to the eye through the interface surface.

11. The system of claim 10, wherein the covering forms an enclosure over a portion of the conducting element and the applicator further comprises a coolant delivery system, the coolant delivery system being configured to deliver coolant within the enclosure to cool the interface surface of the covering and the eye, and the enclosure being configured to prevent the coolant from directly contacting the eye.

12. The system of claim 7, wherein the energy supplied to the applicator is a microwave energy.

* * * * *